United States Patent
Combier et al.

(10) Patent No.: US 12,185,682 B2
(45) Date of Patent: *Jan. 7, 2025

(54) METHOD FOR PROMOTING NODULATION IN PLANTS

(71) Applicants: UNIVERSITE TOULOUSE III-PAUL SABATIER, Toulouse (FR); CENTRE NATIONAL DE LA RECHERCHE SCIENTIFIQUE, Paris (FR)

(72) Inventors: Jean-Philippe Combier, Castanet Tolosan (FR); Olivier Andre, Castanet-Tolosan (FR)

(73) Assignees: UNIVERSITE TOULOUSE III-PAUL SABATIER, Toulouse (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 706 days.

This patent is subject to a terminal disclaimer.

(21) Appl. No.: 17/212,354

(22) Filed: Mar. 25, 2021

(65) Prior Publication Data
US 2021/0212281 A1    Jul. 15, 2021

Related U.S. Application Data

(63) Continuation of application No. 15/559,846, filed as application No. PCT/FR2016/050674 on Mar. 24, 2016, now Pat. No. 10,959,393.

(30) Foreign Application Priority Data

Mar. 24, 2015 (FR) ..................... 15/52461

(51) Int. Cl.
| | |
|---|---|
| C12N 15/82 | (2006.01) |
| A01H 17/00 | (2006.01) |
| A01N 65/20 | (2009.01) |
| C07K 7/08 | (2006.01) |
| C12N 1/20 | (2006.01) |

(52) U.S. Cl.
CPC ............ *A01H 17/00* (2013.01); *A01N 65/20* (2013.01); *C07K 7/08* (2013.01); *C12N 1/20* (2013.01); *C12N 15/8261* (2013.01)

(58) Field of Classification Search
None
See application file for complete search history.

(56) References Cited

FOREIGN PATENT DOCUMENTS

| | | |
|---|---|---|
| CN | 103 695 432 A | 4/2014 |
| FR | 1360 727 A | 8/1964 |
| FR | 3 012 471 A1 | 5/2015 |

OTHER PUBLICATIONS

GenBank Accession JM675754, dated Nov. 23, 2011. (Year: 2011).*
Wang et al. (The Plant Cell, vol. 26: 4782-4801, Dec. 2014). (Year: 2014).*
Wang Youning et al: "Soybean miR172c Targets the Repressive AP2 Transcription Factor NNC1 to Activate ENOD40 Expression and Regulate Nodule Initiation", Plant Cell, vol. 26, No. 12, Dec. 2014 (Dec. 1, 2014), pp. 4782-4801, XP002753717.
Bardou F et al: "Dual RNAs in plants", BIOCHIMIE, vol. 93, No. 11, Nov. 1, 2011 (Nov. 1, 2011), Masson, Paris, FR, pp. 1950-1954, XP002734738, ISSN: 0300-9084, [retrieved on Jul. 31, 2011], DOI: 10.1016/J_BIOCHI.2011.07.028.
VOINNET: "Origin, Biogenesis, and Activity of Plant MicroRNAs", CELL, vol. 136, No. 4, Feb. 20, 2009 (Feb. 20, 2009), Cell Press, US, pp. 669-687, XP008112762, ISSN: 0092-8674, DOI: 10.1016/J_ :; ELL.2009.01 .046.
Wang Youning et al: "MicroRNA167-Directed Regulation of the Auxin Response Factors GmARF8a and 3mARF8b Is Required for Soybean Nodulation and Lateral Root Development", Jul. 2015, Plant Physiology Rockville), vol. 168, NR. 3, pp. 101-116, ISSN: 0032-0889(print), XP002760677.
Couzigou Jean-Malo et al: "miRNA-encoded peptides (miPEPs): A new tool to analyze the roles of miRNAs in plant biology", RNA Biology, vol. 12, No. 11, Nov. 2015 (Nov. 11, 2015), pp. 1178-1180, XP002753719, ISSN: 1547-1180, DOI: 10.1080/15476286.2015. 1094601.
Dominique Lauressergues et al: "Primary transcripts of microRNAs encode regulatory peptides", Nature, ,01. 520, No. 7545, Mar. 25, 2015 (Mar. 25, 2015), United Kingdom, pp. 90-93, XP055225397, ISSN: 0028-0836, DOI: 10.1038/nature14346.
Nova-Franco et al: "The miR172c-AP2-1 Node as a Key Regulator of the Common Bean—Rhizobia Nitrogen Fixation Symbiosis", Plant Physiol., Mar. 2015 (Mar. 1, 2015).
FR Search Report, dated Feb. 8, 2016, from corresponding FR 1552461 application.
International Search Report, dated Aug. 29, 2016, from corresponding PCT/FR2016/050674 application.
Brown, et al. (Plant Physiology 85.1 (1987): 120-123). (Year: 1987).
Perez-Montano, F., et al. (Microbiological research 169.5-6 (2014): 325-336. (Year: 2014).

* cited by examiner

*Primary Examiner* — Charles Logsdon
(74) *Attorney, Agent, or Firm* — Maier & Maier, PLLC

(57) ABSTRACT

Micropeptides (miPEPs), or peptides coded by microRNAs, for promoting nodulation between a plant and a bacterium, as well as their use in this manner.

20 Claims, 5 Drawing Sheets

Figure 1:
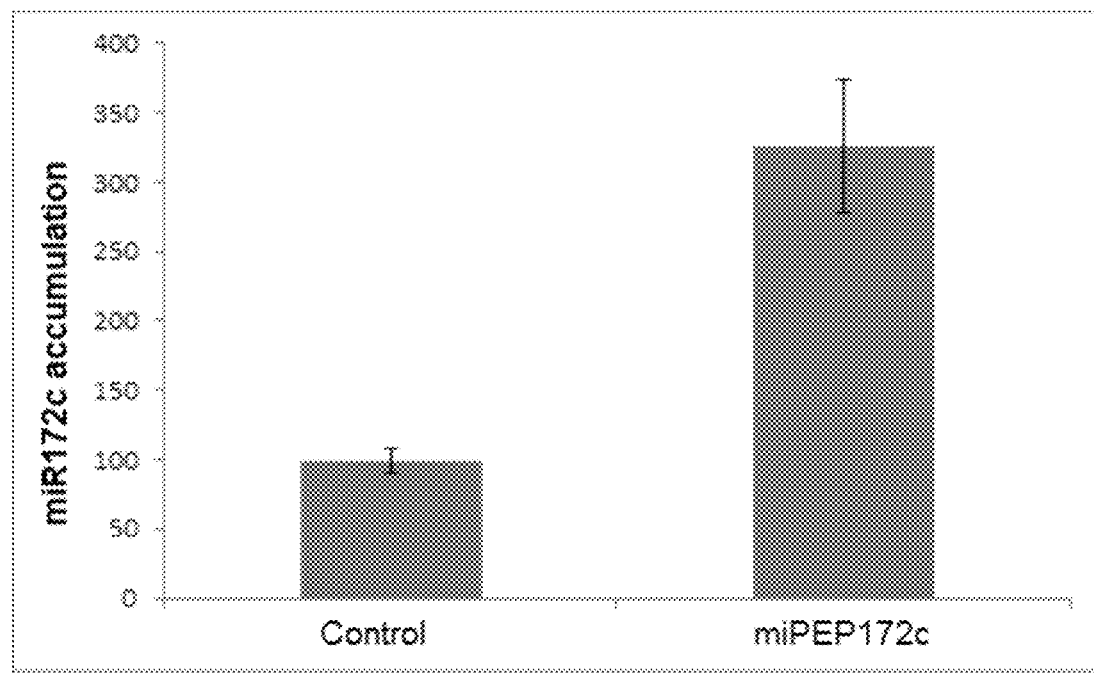

Specification includes a Sequence Listing.

METHOD FOR PROMOTING NODULATION IN PLANTS

The present invention relates to the use of micropeptides (peptides coded by microRNAs or "miPEPs") for promoting nodulation in plants.

In plants, the acquisition of nutrients from the soil is of great importance and can constitute a limitation to the development of plants. Some plants have thus developed an ability to establish symbiotic relationships with microorganisms present in the soil with the objective of improving the acquisition of nutrients.

Leguminous plants, for example, are capable of establishing a symbiosis with bacteria from the Rhizobiaceae family. The host plant and the bacterium will in this way be recognisable to one another by way of an exchange of molecular signals. The plant will especially produce flavonoids which will introduce the expression of specific genes in the bacterium, leading to the production of lipochito-oligosaccharide compounds, i.e. Nod factors, which are the cause of numerous developmental changes in the host plant. The bacteria will then penetrate the hairs of the roots of the plants and induce the formation of nodules. This mechanism of colonisation of the plant by the bacterium is referred to as "nodulation".

The plant then provides the bacteria both with nutrients and a source of energy in the form of adenosine triphosphate (ATP) generated by photosynthesis. In return, the bacteria fix atmospheric nitrogen in the form of ammonium, thus providing an important source of nitrogen digestible by the plant.

Nitrogen is a nutrient of which the provision has often proven to be decisive for the growth of plants. Generally, the greater is the fixation of nitrogen in plants, the greater are the harvests. Consequently, the rate of nodulation of plants is very often linked to a greater harvest. Efficient nodulation of plants also makes it possible to reduce the amounts of fertiliser and to fertilise soils with nitrogenous compounds digestible by the plants. In addition, the content of proteins is also greater in leguminous plants compared to other plant families due to the fixation of nitrogen by the bacteria. The increased content of proteins thus makes leguminous plants particularly beneficial both for human consumption and for animal feed.

The inoculation of plants with specific strains of bacteria makes it possible to promote nodulation. Nevertheless, although different techniques are available, inoculation has often proven to be ineffective. Consequently, it is necessary to provide a simple treatment to improve the nodulation of plants.

MicroRNAs (miRs) are small non-coding RNAs of approximately 21 nucleotides once mature, which control the expression of target genes at post-transcriptional level by breaking down the target mRNA or by inhibiting the translation thereof. The miRs are especially found in plants, and the genes targeted by the miRs are often key genes of developmental processes.

The regulation of the expression of miRs is very poorly understood, but it has been found that it involves, like most coding genes, an RNA polymerase II: this enzyme produces a primary transcript, referred to as "pri-miR", which is then matured by a protein complex containing Dicer-type enzymes especially. This maturation leads firstly to the formation of a miR precursor referred to as a "pre-miR", having a stem-loop secondary structure containing the miR and its complementary sequence miR*. The precursor is then matured, which leads to the formation of a shorter double-stranded RNA containing the miR and the miR*. The miR is then manipulated by the RISC complex, which cleaves the mRNA from the target gene or inhibits the translation thereof.

Especially, miR172c has been identified in leguminous plants such as alfalfa, trefoil, soybean and common bean (Lelandais-Brière et al., Genome-wide *Medicago truncatula* small RNA analysis revealed novel microRNAs and isoforms differentially regulated in roots and nodules, *Plant Cell* 21: 2780-2796, 2009; Wang et al., Identification and expression analysis of miRNAs from nitrogen-fixing soybean nodules, *Biochem Biophys Res Commun* 378: 799-803, 2009; Valdes-Lopez et al., Essential role of MYB transcription factor: PvPHR1 and microRNA: PvmiR399 in phosphorus deficiency signalling in common bean roots, *Plant Cell Environ* 31: 1834-1843, 2008; De Luis et al., Two microRNAs linked to nodule infection and nitrogen-fixing ability in the legume *Lotus japonicus, Plant Physiol* 160: 2137-2154, 2012).

Recently, it has been shown that miR172c regulates the formation of nodules by reducing the expression of its target gene NNC1 (Nodule Number Control 1), a transcription factor of the gene AP2, which reduces the expression of the gene NOD40, which is essential in the process of nodulation in soybeans (Wang et al., Soybean miR172c targets the repressive AP2 transcription factor NNC1 to activate ENOD40 expression and regulate module initiation, *Plant Cell* 26: 4782-4801, 2014). Another recent study has also shown that a rise in the amount of miR172c leads to a rise in nodulation and nitrogen fixation in the common bean (Nova-Franco et al., The miR172c-AP2-1 Node as a Key Regulator of the Common Bean—Rhizobia Nitrogen Fixation Symbiosis, *Plant Physiol*. doi:10.1104/pp. 114.255547, March 2015).

Until now, miRs, and by extension their primary transcript, have always been regarded, based on their particular mode of action, as non-coding regulatory RNAs that do not produce any peptide. However, the inventors have recently demonstrated in patent application FR 13/60727 the existence of micropeptides (or "miPEPs", microRNA coded PEPtides) capable of modulating the accumulation of miRs in cells.

In this context, the object of the present invention is to propose new effective and ecological tools for promoting nodulation in plants.

One of the aspects of the invention is to propose a new use of miPEPs for promoting nodulation between a plant and a bacterium.

Another aspect of the invention relates to a miPEP making it possible to promote the nodulation of plants.

Another aspect of the invention also relates to a new method for culturing plants in symbiosis with a bacterium.

Another aspect of the invention is to propose a composition of miPEPs making it possible to promote nodulation between a plant and a bacterium.

The invention also relates to a transgenic plant and transgenic plant parts, method for producing same, and organs, cells and seeds of transgenic plants, ecologically modified plants, and bacterial innocula.

The invention therefore relates to the use of a peptide for promoting nodulation between a plant and a bacterium, said peptide being introduced into the plant, said peptide having an amino acid sequence comprising or consisting of a sequence identical to that of a miPEP naturally present in said plant, said miPEP naturally present in said plant being a peptide of from to 100 amino acids, especially from 4 to 100 amino acids, of which the sequence is coded by an open reading frame at the primary transcript of a miR, said miPEP being capable of modulating the accumulation of said miR in said plant, which miR regulates the expression of at least one gene involved in the nodulation in said plant.

The inventors have surprisingly and unexpectedly found that the use of peptides of which the sequence comprises or consists of a sequence identical to that of miPEPs coded at the primary transcripts of miRs makes it possible to promote nodulation between a plant and a bacterium.

In the invention, the terms "microRNA", "non-coding mircoRNA" and "miR" are equivalent and may be used interchangeably. They define small molecules of RNA of about 21 nucleotides, which are not translated and do not lead to a peptide or a protein. However, in this mature form, the miRs perform a function of regulation of certain genes via post-transcriptional mechanisms, for example by means the RSIC complex.

The "primary transcript of the miR" (or "pri-miR") corresponds to the RNA molecule obtained directly from transcription of the DNA molecule. Generally, this primary transcript undergoes one or more post-transcriptional modifications, involving for example an especial structure of the RNA or cleavage of certain portions of the RNA by splicing phenomena, and which lead to the precursor form of the miR or ("pre-miR"), then to the mature form of the miR.

The terms "micropeptides" and "miPEPs" (microRNA coded PEPtides) are equivalent and may be used interchangeably. They define a peptide that is coded by an open reading frame present on the primary transcript of a miR and that is capable of modulating the accumulation of said miR. The miPEPs in the sense of the present invention are not to be understood as necessarily being small peptides, as "micro" does not correspond to the size of the peptide. As indicated in patent application FR 13/60727, of which the disclosure should be considered as forming part of the present application, the miPEPs are peptides:
- of from 4 to 100 amino acids, preferably from 4 to 60 amino acids, especially from 4 to 59 amino acids,
- coded by an open reading frame contained in the primary transcript of a miR, preferably in the 5' portion of the primary transcript of said miR, and
- capable of modulating the accumulation of said miR in a eukaryotic cell.

The terms "open reading frame" or "ORF" are equivalent and may be used interchangeably. They correspond to a sequence of nucleotides in a DNA or RNA molecule that may potentially code a peptide or a protein: said open reading frame begins with a start codon (the start codon generally coding a methionine), followed by a series of codons (each codon coding an amino acid), and ends with a stop codon (the stop codon not being translated). Within the scope of the invention, the ORFs may be called specifically "miORFs" when they are present on the primary transcripts of miR.

The miORFs as defined in the invention can have a size of from 15 to 303 nucleotides. An amino acid being coded by a codon of 3 nucleotides, the miORFs having from 15 to 303 nucleotides code miPEPs having from 4 to 100 amino acids.

Especially, the miORFs have a size of:
15, 18, 21, 24, 27, 30, 33, 36, 39, 42, 45, 47, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153, 156, 159, 162, 165, 168, 171, 174, 177, 180, 183, 186, 189, 192, 195, 198, 201, 204, 207, 210, 213, 216, 219, 222, 225, 228, 231, 234, 237, 240, 243, 246, 249, 252, 255, 258, 261, 264, 267, 270, 273, 276, 279, 282, 285, 288, 291, 294, 297, 300 or 303 nucleotides and code, respectively, miPEPs having a size of:
4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 amino acids.

A miPEP can also have a size of from 3 to 100 amino acids.

Taking into account the degeneracy of the genetic code, one and the same miPEP is or may be coded by several nucleotide sequences. Nucleotide sequences of this kind, differing from one another by at least one nucleotide but coding one and the same peptide, are called "degenerate sequences".

In the invention, the term "plant" refers generally to all or part of a plant, whatever its stage of development (including the plant in the form of a seed or young shoot), to one or more organs of the plant (such as the leaves, the roots, the stem, the flowers), to one or more cells of the plant, or also to a cluster of cells of the plant.

The term "nodulation" refers to the colonisation of a plant by a symbiotic bacterium resulting in the formation of nodules on the roots.

In a non-limiting manner, the parameters making it possible to determine and quantify the nodulation between a plant and a bacterium can be, especially:
- the size and the number of the nodules,
- the nitrogen content in all or part of the plant,
- or, indirectly, the development of some parts of the plant, such as the pods or the roots.

The "nodules" can also be called "nodosities". These are swellings that form on the roots of the plants under the action of bacteria. Their size and number can be measured with the naked eye or by microscope using techniques known to a person skilled in the art. Their size is measured after a long period of culture (greater than 30 days) by measuring the size of nodules on the basis of photographs, for example with the aid of ImageJ type software.

The "nitrogen content" corresponds to the concentration of nitrogen in the plant or in part of the plant. For example, it can be the concentration of nitrogen in the aerial parts in g of nitrogen per kg of dry leaf weight. This concentration of nitrogen can be determined by techniques known to a person skilled in the art. For example, one method consists of burning a sample of known mass at an elevated temperature (approximately 900° C.) in the presence of oxygen, leading to a release of carbon dioxide, water, and nitrogen. The gases are then passed over particular columns (such as an aqueous potassium hydroxide solution), which absorb the carbon dioxide and water. A column containing a detector of thermal conductivity at the end is then used to separate the nitrogen from all residual carbon dioxide and the water, and the content of residual nitrogen is quantified.

The "development of some parts of the plant" corresponds to the growth or to the maturation of some parts of the plant. The development of some parts of the plant can be determined for example by measuring the rate of growth or the size or the weight of some parts of the plant. This parameter can be easily measured by taking, for example, measurements of the dry weight of the roots, pods, or aerial parts of the plant.

In addition, within the scope of the invention, the expression "promote nodulation" or "improve nodulation" means:
- either an acceleration of the nodulation (for example a quicker formation of the nodules in a given plant compared to a reference plant),
- or an increase of the nodulation (for example a greater number or a greater size of the nodules in a given plant compared to a reference plant),
- or an acceleration and an increase of the nodulation.

It is important to note that the use according to the invention has the advantage of being ecological because the miPEP is a peptide that is naturally present in the plant.

The invention also relates to the use of a miPEP introduced exogenously into a plant to promote nodulation between said plant and a bacterium,
- said miPEP introduced exogenously being a peptide comprising or consisting of a sequence identical to that of a miPEP naturally present in said plant,
- which naturally present miPEP is a peptide of from 3 to 100 amino acids, especially from 4 to 100 amino acids, of which the sequence is coded by an open reading frame at the 5' portion of the primary transcript of a miR,
- said miPEP being capable of modulating the accumulation of said miR in said plant, which miR regulates the expression of at least one gene involved in the nodulation in said plant,
- the sum of the amount of said miPEP introduced exogenously and of the amount of said naturally present miPEP being strictly greater than the amount of said naturally present miPEP.

Within the scope of the invention, the expression "miPEP introduced exogenously" refers to a miPEP introduced artificially into the plant, whether or not it exists naturally in the plant. The introduction of a miPEP exogenously into the plant thus implies a technical step, which step is not a natural phenomenon and corresponds neither to a crossbreeding nor to a selection.

The miPEP introduced exogenously can be either a peptide produced outside the plant (for example an isolated and/or purified peptide, a synthetic peptide, or a recombinant peptide), or a peptide produced in the plant following the non-natural introduction of a nucleic acid coding said miPEP in said plant.

If the miPEP exists naturally in the plant, it is a "miPEP of endogenous origin".

If the miPEP does not exist naturally in the plant, it is a "miPEP of exogenous origin".

When a "miPEP of exogenous origin" is introduced into the plant, it is then necessary to also introduce the corresponding miR and its primary transcript.

The plant into which the miPEP has not been introduced has a basal quantity of said miPEP, which corresponds to that of said naturally present miPEP. The use of a miPEP comprising or consisting of a sequence identical to that of said miPEP leads to a rise in the total amount of miPEP, which modulates the accumulation of the miR of which the primary transcript contains the sequence coding said miPEP.

In addition, the miPEP introduced can be found in the plant and its introduction has no impact on the stability thereof.

Within the scope of the invention, the term "accumulation" means the production of a molecule, such as a miR or a miPEP, in the cell.

Thus, the "modulation of the accumulation" of a molecule in a cell corresponds to a modification of the quantity of this molecule in the cell.

In addition, the effect of a miPEP can be observed via the modulation of the accumulation of the miR, but also by means of the modulation of the accumulation of the pri-miR or the corresponding pre-miR.

In one embodiment, the invention relates to the use as defined above in which the modulation of the accumulation of said miR is a decrease or an increase of the accumulation of said miR, especially an increase.

A "decrease of the accumulation of the miR" corresponds to a reduction of the amount of said molecule in the cell.

By contrast, an "increase of the accumulation of the miR" corresponds to a rise in the amount of said molecule in the cell.

In one embodiment, the invention relates to the use as defined above in which said gene involved in the nodulation codes a transcription factor of the AP2 family.

In one embodiment, the invention relates to the use as defined above in which said gene involved in the nodulation is the transcription factor NNC1.

In one embodiment, the invention relates to the use as defined above in which said gene involved in the nodulation is the gene NSP1.

In one embodiment, the invention relates to the use as defined above in which said gene involved in the nodulation is the gene NIN.

In one embodiment, the invention relates to the use as defined above in which said gene involved in the nodulation is the gene ENOD40-1.

In one embodiment, the invention relates to the use as defined above in which said gene involved in the nodulation is the gene Hb2.

In one embodiment, the invention relates to the use as defined above in which said gene involved in the nodulation is the gene nifH.

Especially, the invention relates to the use as defined above in which said miR172c has a nucleotide sequence having at least 80% identity, preferably at least 90% identity, with the nucleotide sequence SEQ ID NO: 1.

In one embodiment, the invention relates to the use as defined above in which said miRNA is miR172c, especially in which said miR172c has a nucleotide sequence comprising or consisting of SEQ ID NO: 1.

Especially, the invention relates to the use as defined above in which said miPEP172c has an amino acid sequence having at least 80% identity, preferably at least 90% identity, with the amino acid sequence SEQ ID NO: 2.

In one embodiment, the invention relates to the use as defined above in which said miPEP is miPEP172c, especially in which said miPEP172c has an amino acid sequence comprising or consisting of SEQ ID NO: 2.

Especially, the invention relates to the use as defined above in which said miR167c has a nucleotide sequence having at least 80% identity, preferably at least 90% identity, with the nucleotide sequence SEQ ID NO: 6.

In one embodiment, the invention relates to the use as defined above in which said miRNA is miR167c, especially in which said miR167c has a nucleotide sequence comprising or consisting of SEQ ID NO: 6.

Especially, the invention relates to the use as defined above in which said miPEP167c has an amino acid sequence having at least 80% identity, preferably at least 90% identity, with the amino acid sequence SEQ ID NO: 7.

In one embodiment, the invention relates to the use as defined above in which said miPEP is miPEP167c, especially in which said miPEP167c has an amino acid sequence comprising or consisting of SEQ ID NO: 7.

In one embodiment, the invention relates to the use as defined above in which said plant is a leguminous plant, such as lotus (*Lotus* sp), soybean (*Glycine max*), peanut (*Arachis hypogaea*), common bean (*Phaseolus vulgaris*), pea (*Pisum sativum*), lentil (*Lens culinaris*), chickpea (*Cicer arietinum*), broad bean and field bean (*Vicia faba*), vetches (*Vicia* sp.), vetchlings (*Lathyrus* sp.), alfalfa (*Medicago* sp.), clover (*Trifolium* sp.), lupin (*Lupinus* sp.), mungo bean (*Vigna radiata*), liquorice (*Glycyrrhiza glabra*), rosewood (*Dalbergia*), trefoil (*Lotus corniculatus*), sainfoin (*Onobrychis viciifolia*), rooibos (*Aspalathus linearis*), or fenugreek (*Trigonella foenum-graecum*).

In one embodiment, the invention relates to the use as defined above in which said plant is sugar beet (*Beta vulgaris*).

In one embodiment, the invention relates to the use as defined above in which said plant is selected from *Medicago truncatula*, *M. sativa* and *Glycine max*.

In one embodiment, the invention relates to the use as defined above in which said plant is *Glycine max*.

In one embodiment, the invention relates to the use as defined above in which said bacterium is a bacterium from the Rhizobiaceae family.

In an especial embodiment, the invention relates to the use as defined above in which said bacterium is selected from the genera *Rhizobium*, *Sinorhizobium*, *Mesorhizobium*, *Bradyrhizobium* or *Azorhizobium*.

Within the scope of the invention, said bacterium can also be selected from:

*Rhizobium alamii*, *Rhizobium alkalisoli*, *Rhizobium cellulosilyticum*, *Rhizobium daejeonense*, *Rhizobium endophyticum*, *Rhizobium etli*, *Rhizobium galegae*, *Rhizobium gallicum*, *Rhizobium giardinii*, *Rhizobium hainanense*, *Rhizobium herbae*, *Rhizobium huautlense*, *Rhizobium indigoferae*, *Rhizobium leguminosarum*, *Rhizobium loessense*, *Rhizobium lusitanum*, *Rhizobium mesosinicum*, *Rhizobium miluonense*, *Rhizobium mongolense*, *Rhizobium multihospitium*, *Rhizobium oryzae*, *Rhizobium phaseoli*, *Rhizobium pisi*, *Rhizobium tibeticum*, *Rhizobium sullae*, *Rhizobium tropici*, *Rhizobium tubonense*, *Rhizobium undicola*, *Rhizobium vignae*, *Rhizobium yanglingense*,

*Mesorhizobium albiziae*, *Mesorhizobium alhagi*, *Mesorhizobium amorphae*, *Mesorhizobium australicum*, *Mesorhizobium camelthorni*, *Mesorhizobium caraganae*, *Mesorhizobium chacoense*, *Mesorhizobium cicero*, *Mesorhizobium gobiense*, *Mesorhizobium huakuii*, *Mesorhizobium loti*, *Mesorhizobium mediterraneum*, *Mesorhizobium metallidurans*, *Mesorhizobium opportunistum*, *Mesorhizobium plurifarium*, *Mesorhizobium robiniae*, *Mesorhizobium shangrilense*, *Mesorhizobium septentrionale*, *Mesorhizobium tarimense*, *Mesorhizobium temperatum*, *Mesorhizobium tianshanense*

*Ensifer abri*, *Sinorhizobium americanum*, *Ensifer arboris*, *Ensifer fredii*, *Ensifer garamanticus*, *Ensifer indiaense*, *Ensifer kostiensis*, *Ensifer kummerowiae*, *Ensifer medicae*, *Ensifer meliloti*, *Ensifer mexicanus*, *Sinorhizobium morelense*, *Ensifer adhaerens*, *Ensifer numidicus*, *Ensifer saheli*, *Ensifer sojae*, *Ensifer terangae*,

*Bradyrhizobium canariense*, *Bradyrhizobium denitrificans*, *Bradyrhizobium elkanii*, *Bradyrhizobium iriomotense*, *Bradyrhizobium japonicum*, *Bradyrhizobium jicamae*, *Bradyrhizobium liaoningense*, *Bradyrhizobium pachyrhizi*, *Bradyrhizobium yuanmingense*

*Burkholderia caribensis*, *Burkholderia cepacia*, *Burkholderia mimosarum*, *Burkholderia nodosa*, *Burkholderia phymatum*, *Burkholderia sabiae*, *Burkholderia tuberum*

*Phyllobacterium trifolii*, *Phyllobacterium ifriqiyense*, *Phyllobacterium leguminum*

*Microvirga lupine*, *Microvirga lotononidis*, *Microvirga zambiensis*

*Azorhizobium caulinodans*, *Azorhizobium doebereinerae*

*Ochrobactrum cytisi*, *Ochrobactrum lupini*

*Methylobacterium nodulans*,

*Cupriavidus taiwanensis*,

*Devosia neptuniae*,

*Shinella kummerowiae*.

In one embodiment, the invention relates to the use as defined above in which said bacterium is a bacterium selected from *Rhizobium leguminosarum*, *Rhizobium etli*, *Rhizobium tropici*, *Rhizobium galegae*, *Sinorhizobium* sp. NGR234, *Sinorhizobium meliloti*, *Sinorhizobium Sinorhizobium saheli*, *Sinorhizobium teranga*, *Mesorhizobium ciceri*, *Mesorhizobium huakuii*, *Mesorhizobium loti*, *Bradyrhizobium elkanii*, *Bradyrhizobium japonicum*, *Bradyrhizobium lupini*, *Bradyrhizobium* sp. "cowpea" and *Azorhizobium caulinodans*.

Especially, the bacterium *Rhizobium elti* allows the nodulation of the common bean.

Especially, the bacterium *Rhizobium leguminosarum* allows the nodulation of pea, alfalfa, sugar beet, vetches, and lentil.

Especially, the bacterium *Rhizobium pisi* allows the nodulation of pea, common bean, and vetches.

Especially, the bacterium *Rhizobium phaseoli* allows the nodulation of dry common bean and of common bean.

Especially, the bacterium *Rhizobium fabae* allows the nodulation of broad bean.

Especially, the bacterium *Rhizobium ciceri* allows the nodulation of chickpea.

Especially, the bacterium *Rhizobium trifoli* allows the nodulation of clover.

Especially, the bacterium *Sinorhizobium meliloti* allows the nodulation of alfalfa, fenugreek, or melilotus.

Especially, the bacterium *Sinorhizobium fredii* allows the nodulation of soybean.

Especially, the bacterium *Mesorhizobium loti* allows the nodulation of lotus, clover, lupin, or chickpea.

Especially, the bacterium *Bradyrhizobium japonicum* allows the nodulation of soybean.

Especially, the bacterium *Bradyrhizobium* sp. *Vigna* allows the nodulation of peanut.

Especially, the bacterium *Bradyrhizobium* sp. *Arachis* allows the nodulation of peanut.

In one embodiment, the invention relates to the use as defined above for promoting nodulation between a *Glycine max* plant and a *Bradirhizobium japonicum* bacterium, in which miPEP172c is introduced exogenously into said *Glycine max* plant, said miPEP172c also being naturally present in said *Glycine max* plant, said miPEP172c introduced exogenously being a peptide of which the sequence comprises or consists of a sequence identical to that of said naturally present miPEP172c, said sequence of the naturally present miPEP172c being coded by an open reading frame at the 5' portion of the primary transcript of miR172c, which miR172c regulates the expression of at least one gene involved in the nodulation in *Glycine max*, the sum of the amount of said miPEP172c introduced exogenously and of the amount of said naturally present miPEP172c being strictly greater than the amount of said miPEP172c naturally present in said *Glycine max* plant.

In one embodiment, the invention relates to the use of a miPEP to promote nodulation between a *Glycine max* plant and a *Bradirhizobium japonicum* bacterium, in which miPEP172c is introduced exogenously into said *Glycine max* plant, said miPEP172c being naturally present in said *Glycine max* plant,
  said miPEP172c introduced exogenously being a peptide of which the sequence has at least 80% identity, preferably at least 90% identity, with the sequence SEQ ID NO: 2, said sequence of the naturally present miPEP172c being coded by an open reading frame at the 5' portion of the primary transcript of the miR172c, which miR172c regulates the expression of at least one gene involved in the nodulation in *Glycine max*,
  the sum of the amount of said miPEP172c introduced exogenously and of the amount of said naturally present miPEP172c being strictly greater than the amount of said miPEP172c naturally present in said *Glycine max* plant.

In one embodiment, the invention relates to the use of a miPEP to promote nodulation between a *Glycine max* plant and a *Bradirhizobium japonicum* bacterium, in which miPEP172c is introduced exogenously into said *Glycine max* plant, said miPEP172c being naturally present in said *Glycine max* plant,
  said miPEP172c introduced exogenously being a peptide of which the sequence comprises or consists of SEQ ID NO: 2, said sequence of the naturally present miPEP172c being coded by an open reading frame at the 5' portion of the primary transcript of the miR172c, which miR172c regulates the expression of at least one gene involved in the nodulation in *Glycine max*,
  the sum of the amount of said miPEP172c introduced exogenously and of the amount of said naturally present miPEP172c being strictly greater than the amount of said miPEP172c naturally present in said *Glycine max* plant.

In one embodiment, the invention relates to the use of a miPEP to promote nodulation between a *Glycine max* plant and a *Bradirhizobium japonicum* bacterium, in which miPEP172c is introduced exogenously into said *Glycine max* plant, said miPEP172c being naturally present in said *Glycine max* plant,
  said miPEP172c introduced exogenously being a peptide of which the sequence comprises or consists of a sequence identical to that of said naturally present miPEP172c, said sequence of the naturally present miPEP172c being coded by an open reading frame at the 5' portion of the primary transcript of the miR172c, which miR172c regulates the expression of at least one gene involved in the nodulation in *Glycine max*,
  which miR172c comprises or consists of SEQ ID NO: 1,
  the sum of the amount of said miPEP172c introduced exogenously and of the amount of said naturally present miPEP172c being strictly greater than the amount of said miPEP172c naturally present in said *Glycine max* plant.

In one embodiment, the invention relates to the use as defined above for promoting nodulation between a *Glycine max* plant and a *Bradirhizobium japonicum* bacterium, in which miPEP167c is introduced exogenously into said *Glycine max* plant, said miPEP167c being naturally present in said *Glycine max* plant,
  said miPEP167c introduced exogenously being a peptide of which the sequence comprises or consists of a sequence identical to that of said naturally present miPEP167c, said sequence of the naturally present miPEP167c being coded by an open reading frame at the 5' portion of the primary transcript of the miR167c, which miR167c regulates the expression of at least one gene involved in the nodulation in *Glycine max*,
  the sum of the amount of said miPEP167c introduced exogenously and of the amount of said naturally present miPEP167c being strictly greater than the amount of said miPEP167c naturally present in said *Glycine max* plant.

In one embodiment, the invention relates to the use of a miPEP to promote nodulation between a *Glycine max* plant and a *Bradirhizobium japonicum* bacterium, in which miPEP167c is introduced exogenously into said *Glycine max* plant, said miPEP167c being naturally present in said *Glycine max* plant,
  said miPEP167c introduced exogenously being a peptide of which the sequence has at least 80% identity, preferably at least 90% identity, with the sequence SEQ ID NO: 7, said sequence of the naturally present miPEP167c being coded by an open reading frame at the 5' portion of the primary transcript of the miR167c, which miR167c regulates the expression of at least one gene involved in the nodulation in *Glycine max*,
  the sum of the amount of said miPEP167c introduced exogenously and of the amount of said naturally present miPEP167c being strictly greater than the amount of said miPEP167c naturally present in said *Glycine max* plant.

In one embodiment, the invention relates to the use of a miPEP to promote nodulation between a *Glycine max* plant and a *Bradirhizobium japonicum* bacterium, in which miPEP167c is introduced exogenously into said *Glycine max* plant, said miPEP167c being naturally present in said *Glycine max* plant,
  said miPEP167c introduced exogenously being a peptide of which the sequence comprises or consists of SEQ ID NO: 7, said sequence of the naturally present miPEP167c being coded by an open reading frame at the 5' portion of the primary transcript of the miR167c, which miR167c regulates the expression of at least one gene involved in the nodulation in *Glycine max*,
  the sum of the amount of said miPEP167c introduced exogenously and of the amount of said naturally present miPEP167c being strictly greater than the amount of said miPEP167c naturally present in said *Glycine max* plant.

In one embodiment, the invention relates to the use of a miPEP to promote nodulation between a *Glycine max* plant and a *Bradirhizobium japonicum* bacterium, in which miPEP167c is introduced exogenously into said *Glycine max* plant, said miPEP167c being naturally present in said *Glycine max* plant,
  said miPEP167c introduced exogenously being a peptide of which the sequence comprises or consists of a sequence identical to that of said naturally present miPEP167c, said sequence of the naturally present miPEP167c being coded by an open reading frame at the 5' portion of the primary transcript of the miR167c, which miR167c regulates the expression of at least one gene involved in the nodulation in *Glycine max*,
  which miR167c comprises or consists of SEQ ID NO: 6,
  the sum of the amount of said miPEP167c introduced exogenously and of the amount of said naturally present miPEP167c being strictly greater than the amount of said miPEP167c naturally present in said *Glycine max* plant.

In one embodiment, the invention relates to the use as defined above in which said miPEP is introduced externally into the plant, preferably by watering, spraying, or by the addition of a fertiliser, a soil, a culture substrate, or with the aid of a support in contact with the plant. In one embodiment, the invention relates to the use as defined above in which said miPEP is introduced externally into a grain or a seed, preferably by watering, by spraying, or by the addition of a fertiliser, a soil, a culture substrate, or with the aid of a support in contact with the grain or the seed.

In one embodiment, the invention relates to the use as defined above in which said miPEP is used to treat the plant in grain form.

In one embodiment, the invention relates to the use as defined above in which said miPEP is introduced by watering, especially by spraying.

In one embodiment, the invention relates to the use as defined above in which said miPEP is introduced by watering and by the addition of a fertiliser.

In one embodiment, the invention relates to the use as defined above in which said miPEP is introduced by the addition of a fertiliser.

In one embodiment, the invention relates to the use as defined above in which said miPEP is introduced, by watering, and by the addition of a fertiliser.

In one embodiment, the invention relates to the use as defined above in which said miPEP is introduced by the addition of granules.

The inventors have, in fact, surprisingly found that it is possible to directly apply a composition comprising a miPEP to the plant so as to modulate the accumulation of the corresponding miR in the plant, which indicates that the miPEP is captured by the plant.

In one embodiment, the invention relates to the use as defined above in which the plant is treated with a composition comprising $10^{-9}$ M to $10^{-4}$ M of said miPEP, especially $10^{-9}$ M, $10^{-8}$ M, $10^{-7}$ M, $10^{-6}$ M, $10^{-5}$ M or $10^{-4}$ M of said miPEP.

The compositions preferably have a concentration of from $10^{-8}$ M to $10^{-5}$ M for an application by watering or by spraying onto the plant.

In a complementary manner, compositions that are concentrated to a greater or lesser extent can be envisaged to treat the plant with the miPEP. For example, and in a non-limiting manner, compositions concentrated to a greater extent comprising from $10^{-1}$ M to $10^{-3}$ M, especially $10^{-2}$ M of miPEP, can be used in the case in which the miPEP introduced exogenously is administered to the plant by spreading.

The solubility properties of miPEPs are determined especially by their composition of amino acids. Hydrophilic miPEPs can be solubilised and conditioned in aqueous solutions, such as water. Hydrophobic miPEPs can be solubilised and conditioned in solvents, such as organic solvents.

For a treatment of plants by the miPEPs, the organic solvents are solvents that are not toxic for the plants in low quantities, i.e. they do not have a detrimental effect on the development of the plant. In a non-limiting manner, the organic solvents can be selected from acetonitrile and acetic acid.

The miPEPs can also be solubilised and conditioned in mixtures of organic solvents, such as a mixture of acetonitrile and acetic acid. Especially, the miPEPs can be solubilised in a solution comprising 50% acetonitrile, 10% acetic acid, and 40% water (volume/volume/volume).

Especially, miPEP172c is solubilised in a solution comprising 40% water, 50% acetonitrile, and 10% acetic acid (volume/volume/volume), or in water.

Especially, miPEP167c is solubilised in water.

In one embodiment, the invention relates to the use as defined above in which said miPEP is introduced into the plant by way of a nucleic acid coding said miPEP, said nucleic acid being introduced into the plant.

In one embodiment, the invention relates to the use as defined above in which the number of nodules is increased in the plant in which said miPEP has been introduced compared to the number of nodules of an identical plant of the same age into which no miPEP has been introduced, or compared to the number of nodules of an identical plant of the same age into which said miPEP has not been introduced.

In one embodiment, the invention relates to the use as defined above in which the concentration of nitrogen is increased in the aerial parts of the plant into which said miPEP has been introduced compared to the concentration of nitrogen in the aerial parts of an identical plant of the same age into which no miPEP has been introduced or compared to the nitrogen concentration in the aerial parts of an identical plant of the same age into which said miPEP has not been introduced.

In one embodiment, the invention relates to the use as defined above in which the weight of the pods is increased in the plant into which said miPEP has been introduced compared to the weight of the pods of an identical plant of the same age into which no miPEP has been introduced, or compared to the weight of the pods of an identical plant of the same age into which said miPEP has not been introduced.

The increase of the parameters making it possible to determine and quantify the nodulation in the plant into which the miPEP has been introduced (such as the number of nodules, the nitrogen concentration, or the weight of the pods) is preferably evidenced by comparison with an identical plant (i.e. a plant of the same species and/or variety), of the same age, and cultivated in the same conditions, but into which no miPEP has been introduced.

The invention also relates to the use of a miPEP introduced exogenously into a plant to promote nodulation between said plant and a bacterium,
    said miPEP being coded by the primary transcript, introduced artificially into the plant, of a miR,
    said primary transcript, said miR and said miPEP being naturally absent from said plant,
    said miPEP being capable of modulating the accumulation of said miR in said plant, which miR regulates the expression of at least one gene involved in the nodulation in said plant.

In an especial embodiment, said primary transcript of the miR, the miR and said miPEP are introduced into the plant with the aid of a vector.

In another aspect, the invention relates to a method for promoting the nodulation between a plant and a bacterium, comprising a step of introducing a miPEP into a plant exogenously, said miPEP also being present naturally in said plant,
    said miPEP introduced exogenously being a peptide of from 3 to 100 amino acids, especially from 4 to 100 amino acids, of which the sequence comprises or consists of a sequence identical to that of said naturally present miPEP, which sequence of the naturally present miPEP is coded by an open reading frame at the 5' portion of the primary transcript of a miR, said miPEP being capable of modulating the accumulation of said miR, which miR regulates the expression of at least one gene involved in the nodulation in said plant, the sum of the amount of said miPEP introduced exogenously and of the amount of said naturally present miPEP being strictly greater than the amount of said naturally present miPEP.

In one embodiment, the invention relates to a method as defined above in which said gene involved in the nodulation codes a transcription factor of the AP2 family.

In one embodiment, the invention relates to a method as defined above in which said gene involved in the nodulation is the transcription factor NNC1.

In one embodiment, the invention relates to a method as defined above in which said gene involved in the nodulation is the gene NSP1.

In one embodiment, the invention relates to a method as defined above in which said gene involved in the nodulation is the gene NIN.

In one embodiment, the invention relates to a method as defined above in which said gene involved in the nodulation is the gene ENOD40-1.

In one embodiment, the invention relates to a method as defined above in which said gene involved in the nodulation is the gene Hb2.

In one embodiment, the invention relates to a method as defined above in which said gene involved in the nodulation is the gene nifH.

In one embodiment, the invention relates to a method as defined above in which said miRNA is miR172c, especially in which said miR172c has a nucleotide sequence comprising or consisting of SEQ ID NO: 1.

In one embodiment, the invention relates to a method as defined above in which said miPEP is miPEP172c, especially in which said miPEP172c has an amino acid sequence comprising or consisting of SEQ ID NO: 2.

In one embodiment, the invention relates to a method as defined above in which said miRNA is miR167c, especially in which said miR167c has a nucleotide sequence comprising or consisting of SEQ ID NO: 6.

In one embodiment, the invention relates to a method as defined above in which said miPEP is miPEP167c, especially in which said miPEP167c has an amino acid sequence comprising or consisting of SEQ ID NO: 7.

In one embodiment, the invention relates to a method as defined above in which said plant is a leguminous plant, such as lotus (*Lotus* sp.), soybean (*Glycine max*), peanut (*Arachis hypogaea*), common bean (*Phaseolus vulgaris*), pea (*Pisum sativum*), lentil (*Lens culinaris*), chickpea (*Cicer arietinum*), broad bean and field bean (*Vicia faba*), vetches (*Vicia* sp.), vetchlings (*Lathyrus* sp.), alfalfa (*Medicago* sp.), clover (*Trifolium* sp.), lupin (*Lupinus* sp.), mungo bean (*Vigna radiata*), liquorice (*Glycyrrhiza glabra*), rosewood (*Dalbergia*), trefoil (*Lotus corniculatus*), sainfoin (*Onobrychis viciifolia*), rooibos (*Aspalathus linearis*), or fenugreek (*Trigonella foenum-graecum*).

In one embodiment, the invention relates to a method as defined above in which said plant is sugar beet (*Beta vulgaris*).

In one embodiment, the invention relates to a method as defined above in which said bacterium is a bacterium from the Rhizobiaceae family.

In an especial embodiment, the invention relates to a method as defined above in which said bacterium is selected from the genera *Rhizobium, Sinorhizobium, Mesorhizobium, Bradyrhizobium* or *Azorhizobium*.

In one embodiment, the invention relates to a method as defined above in which said bacterium is a bacterium selected from *Rhizobium leguminosarum, Rhizobium etli, Rhizobium tropici, Rhizobium galegae, Sinorhizobium* sp. NGR234, *Sinorhizobium meliloti, Sinorhizobium fredii, Sinorhizobium saheli, Sinorhizobium teranga, Mesorhizobium ciceri, Mesorhizobium huakuii, Mesorhizobium loti, Bradyrhizobium elkanii, Bradyrhizobium japonicum, Bradyrhizobium lupini, Bradyrhizobium* sp. "cowpea" and *Azorhizobium caulinodans*.

In one embodiment, the invention relates to a method as defined above for promoting nodulation between a *Glycine max* plant and a *Bradirhizobium japonicum* bacterium, in which miPEP172c is introduced exogenously into said *Glycine max* plant, said miPEP172c being naturally present in said *Glycine max* plant, said miPEP172c introduced exogenously being a peptide comprising or consisting of a sequence identical to that of said naturally present miPEP172c, which naturally present miPEP172c is a peptide of from 3 to 100 amino acids of which the sequence is coded by an open reading frame at the 5' portion of the primary transcript of the miR172c, said miPEP172c being capable of increasing the accumulation of said miR172c, which miR172c regulates the expression of at least one gene involved in the nodulation in *Glycine max*, the sum of the amount of said miPEP172c introduced exogenously and of the amount of said naturally present miPEP172c being strictly greater than the amount of said naturally present miPEP172c.

In one embodiment, the invention relates to a method as defined above for promoting nodulation between a *Glycine max* plant and a *Bradirhizobium japonicum* bacterium, in which the miPEP167c is introduced exogenously into said *Glycine max* plant, said miPEP167c being naturally present in said *Glycine max* plant, said miPEP167c introduced exogenously being a peptide comprising or consisting of a sequence identical to that of said naturally present miPEP167c, which naturally present miPEP167c is a peptide of from 3 to 100 amino acids of which the sequence is coded by an open reading frame at the 5' portion of the primary transcript of the miR167c, said miPEP167c being capable of increasing the accumulation of said miR167c, which miR167c regulates the expression of at least one gene involved in the nodulation in *Glycine max*, the sum of the amount of said miPEP167c introduced exogenously and of the amount of said naturally present miPEP167c being strictly greater than the amount of said naturally present miPEP167c.

In one embodiment, the invention relates to a method as defined above in which said miPEP is introduced externally into the plant, preferably by watering, by spraying, or by the addition of a fertiliser, a soil, a culture substrate, or with the aid of a support in contact with the plant.

In one embodiment, the invention relates to a method as defined above in which said miPEP is introduced externally into a plant by the addition of granules.

In one embodiment, the invention relates to a method as defined above in which said miPEP is introduced externally into a grain or seed, preferably by watering, by spraying, or by the addition of a fertiliser, a soil, a culture substrate, or with the aid of a support in contact with the grain or the seed.

In one embodiment, the invention relates to a method as defined above in which said miPEP is used to treat the plant in grain form.

In one embodiment, the invention relates to a method as defined above in which said miPEP is administered to the plant in the form of a composition comprising from $10^{-9}$ M to $10^{-4}$ M of said miPEP, especially $10^{-9}$, $10^{-8}$, $10^{-7}$, $10^{-6}$, $10^{-5}$ or $10^{-4}$ M of said miPEP.

In one embodiment, the invention relates to a method as defined above in which said miPEP is introduced into the plant by way of a nucleic acid coding said miPEP, said nucleic acid being introduced into the plant.

In one embodiment, the invention relates to a method as defined above in which the number of nodules is increased in the plant into which said miPEP has been introduced compared to the number of nodules of an identical plant of the same age into which no miPEP has been introduced, or compared to the number of nodules of an identical plant of the same age into which said miPEP has not been introduced.

In one embodiment, the invention relates to a method as defined above in which the nitrogen concentration is increased in the aerial parts of the plant into which said miPEP has been introduced compared to the nitrogen concentration in the aerial parts of an identical plant of the same age into which no miPEP has been introduced, or compared to the nitrogen concentration in the aerial parts of an identical plant of the same age into which said miPEP has not been introduced.

In one embodiment, the invention relates to a method as defined above in which the weight of the pods is increased in the plant into which said miPEP has been introduced compared to the weight of the pods of an identical plant of the same age into which no miPEP has been introduced, or compared to the weight of the pods of an identical plant of the same age into which said miPEP has not been introduced.

In another aspect, the invention relates to a method for producing a transgenic plant, said method comprising:
  a) a step of introducing a nucleic acid coding a miPEP having from 3 to 100 amino acids, especially from 4 to 100 amino acids, into a plant, or into at least a cell of said plant, in conditions allowing the expression of said miPEP,
said miPEP also being present naturally in said plant, said naturally present miPEP being a peptide of which the sequence is coded by an open reading frame at the 5' portion of the primary transcript of a miR, said miPEP being capable of modulating the accumulation of said miR in the plant, which miR regulates the expression of at least one gene involved in the nodulation, and
  b) a step of culturing the plant, or at least a cell of said plant, obtained in step a) in conditions making it possible to obtain a transgenic plant.

In one embodiment, the invention relates to a method for producing a transgenic plant as defined above in which said transgenic plant obtained in step b) is more capable of nodulation compared to an identical plant into which said nucleic acid has not been introduced.

In one embodiment, the invention relates to a method for producing a transgenic plant as defined above in which the expression of said miPEP coded by the nucleic acid introduced into the plant leads to an improved nodulation compared to an identical plant into which said nucleic acid has not been introduced.

In one embodiment, the invention relates to a method for producing a transgenic plant as defined above in which step a) is performed with the aid of a vector containing said nucleic acid, preferably a plasmid.

In one embodiment, the invention relates to a method for producing a transgenic plant as defined above in which said nucleic acid does not comprise the complete sequence of said miR.

In one embodiment, the invention relates to a method for producing a transgenic plant as defined above in which the expression of said nucleic acid from step a) is placed under the control of a strong promoter, preferably a strong constitutive promoter, such as the promoter 35S.

In one embodiment, the invention relates to a method for producing a transgenic plant as defined above in which said gene involved in the nodulation codes a transcription factor of the AP2 family.

In one embodiment, the invention relates to a method for producing a transgenic plant as defined above in which said gene involved in the nodulation is an endogenous gene and codes a transcription factor of the AP2 family.

In one embodiment, the invention relates to a method for producing a transgenic plant as defined above in which said gene involved in the nodulation codes the transcription factor NNC1.

In one embodiment, the invention relates to a method for producing a transgenic plant as defined above in which said gene involved in the nodulation is an endogenous gene and codes the transcription factor NNC1.

In one embodiment, the invention relates to a method for producing a transgenic plant as defined above in which said gene involved in the nodulation is the gene NSP1.

In one embodiment, the invention relates to a method for producing a transgenic plant as defined above in which said gene involved in the nodulation is an endogenous gene NSP1.

In one embodiment, the invention relates to a method for producing a transgenic plant as defined above in which said gene involved in the nodulation is the gene NIN.

In one embodiment, the invention relates to a method for producing a transgenic plant as defined above in which said gene involved in the nodulation is an endogenous gene NIN.

In one embodiment, the invention relates to a method for producing a transgenic plant as defined above in which said gene involved in the nodulation is the gene ENOD40-1.

In one embodiment, the invention relates to a method for producing a transgenic plant as defined above in which said gene involved in the nodulation is an endogenous gene ENOD40-1.

In one embodiment, the invention relates to a method for producing a transgenic plant as defined above in which said gene involved in the nodulation is the gene Hb2.

In one embodiment, the invention relates to a method for producing a transgenic plant as defined above in which said gene involved in the nodulation is the endogenous gene Hb2.

In one embodiment, the invention relates to a method for producing a transgenic plant as defined above in which said gene involved in the nodulation is the gene nifH.

In one embodiment, the invention relates to a method for producing a transgenic plant as defined above in which said gene involved in the nodulation is the endogenous gene nifH.

In one embodiment, the invention relates to a method for producing a transgenic plant as defined above in which said miRNA is miR172c, especially in which said miR172c has a nucleotide sequence comprising or consisting of SEQ ID NO: 1.

In one embodiment, the invention relates to a method for producing a transgenic plant as defined above in which said miPEP is miPEP172c, especially in which said miPEP172c has an amino acid sequence comprising or consisting of SEQ ID NO: 2.

In one embodiment, the invention relates to a method for producing a transgenic plant as defined above in which said nucleic acid introduced in step a) comprises a nucleotide sequence consisting of SEQ ID NO: 3.

In one embodiment, the invention relates to a method for producing a transgenic plant as defined above in which said miRNA is miR167c, especially in which said miR167c has a nucleotide sequence comprising or consisting of SEQ ID NO: 6.

In one embodiment, the invention relates to a method for producing a transgenic plant as defined above in which said miPEP is miPEP167c, especially in which said miPEP167c has an amino acid sequence comprising or consisting of SEQ ID NO: 7.

In one embodiment, the invention relates to a method for producing a transgenic plant as defined above in which said nucleic acid introduced in step a) comprises a nucleotide sequence consisting of SEQ ID NO: 8.

In one embodiment, the invention relates to a method as defined above in which said plant is a leguminous plant, such as lotus (*Lotus* sp.), soybean (*Glycine max*), peanut (*Arachis hypogaea*), common bean (*Phaseolus vulgaris*), pea (*Pisum sativum*), lentil (*Lens culinaris*), chickpea (*Cicer arietinum*), broad bean and field bean (*Vicia faba*), vetches (*Vicia* sp.), vetchlings (*Lathyrus* sp.), alfalfa (*Medicago* sp.), clover (*Trifolium* sp.), lupin (*Lupinus* sp.), mungo bean (*Vigna radiata*), liquorice (*Glycyrrhiza glabra*), rosewood (*Dalbergia*), trefoil (*Lotus corniculatus*), sainfoin (*Onobrychis viciifolia*), rooibos (*Aspalathus linearis*), or fenugreek (*Trigonella foenum-graecum*).

In one embodiment, the invention relates to a method as defined above in which said plant is sugar beet (*Beta vulgaris*).

In one embodiment, the invention relates to a method as defined above in which said bacterium is a bacterium from the Rhizobiaceae family.

In an especial embodiment, the invention relates to a method as defined above in which said bacterium is selected from the genera *Rhizobium, Sinorhizobium, Mesorhizobium, Bradyrhizobium* or *Azorhizobium*.

In one embodiment, the invention relates to a method as defined above in which said bacterium is a bacterium selected from *Rhizobium leguminosarum, Rhizobium etli, Rhizobium tropici, Rhizobium galegae, Sinorhizobium* sp. NGR234, *Sinorhizobium meliloti, Sinorhizobium fredii, Sinorhizobium saheli, Sinorhizobium teranga, Mesorhizobium ciceri, Mesorhizobium huakuii, Mesorhizobium loti, Bradyrhizobium elkanii, Bradyrhizobium japonicum, Bradyrhizobium lupini, Bradyrhizobium* sp. "cowpea" and *Azorhizobium caulinodans*.

In one embodiment, the invention relates to a method for producing a transgenic plant as defined above, comprising:
  a) a step of introducing a nucleic acid containing the nucleotide sequence SEQ ID NO: 3, coding miPEP172c consisting of the amino acid sequence SEQ ID NO: 2, into a *Glycine max* plant, or into at least a cell of said *Glycine max* plant, in conditions allowing the expression of miPEP172c,
said miPEP172c being naturally present in said *Glycine max* plant, said naturally present miPEP being a peptide of which the sequence is coded by an open reading frame at the 5' portion of the primary transcript of miR172c, said miPEP172c being capable of modulating the accumulation of said miR172c, which miR172c regulates the expression of at least one gene involved in the nodulation in *Glycine max*, et
  b) a step of culturing the plant, or at least a cell of said plant, obtained in step a) in conditions making it possible to obtain a transgenic *Glycine max* plant.

In one embodiment, the invention relates to a method for producing a transgenic plant as defined above, comprising:
  a) a step of introducing a nucleic acid containing the nucleotide sequence SEQ ID NO: 8, coding the miPEP167c consisting of the amino acid sequence SEQ ID NO: 7, into a *Glycine max* plant, or into at least a cell of said *Glycine max* plant, in conditions allowing the expression of miPEP167c,
said miPEP167c being naturally present in said *Glycine max* plant, said naturally present miPEP being a peptide of which the sequence is coded by an open reading frame at the 5' portion of the primary transcript of the miR167c, said miPEP167c being capable of modulating the accumulation of said miR167c, which miR167c regulates the expression of at least one gene involved in the nodulation in *Glycine max*, and
  b) a step of culturing the plant, or at least a cell of said plant, obtained in step a) in conditions making it possible to obtain a transgenic *Glycine max* plant.

In one embodiment, the invention relates to a production method as defined above in which said miPEP is introduced into the plant by way of a nucleic acid coding said miPEP, said nucleic acid being introduced into the plant.

In one embodiment, the invention relates to a method for producing a transgenic plant as defined above in which the number of nodules is increased in the plant into which said miPEP has been introduced compared to the number of nodules in an identical plant of the same age into which no miPEP has been introduced, or compared to the number of nodules of an identical plant of the same age into which said miPEP has not been introduced.

In one embodiment, the invention relates to a method for producing a transgenic plant as defined above in which the nitrogen concentration is increased in the aerial parts of the plant into which said miPEP has been introduced compared to the nitrogen concentration in the aerial parts of an identical plant of the same age into which no miPEP has been introduced, or compared to the nitrogen concentration in the aerial parts of an identical plant of the same age into which said miPEP has not been introduced.

In one embodiment, the invention relates to a method for producing a transgenic plant as defined above in which the weight of the pods is increased in the plant into which said miPEP has been introduced compared to the weight of the pods of an identical plant of the same age into which no miPEP has been introduced, or compared to the weight of the pods of an identical plant of the same age into which said miPEP has not been introduced.

In one aspect, the invention also relates to a transgenic plant as obtained by the production method as defined above.

In another aspect, the invention relates to a plant into which a miPEP has been introduced according to the above-described use or method for promoting nodulation.

In another aspect, the invention relates to a peptide having an amino acid sequence having at least 80% identity, preferably at least 90% identity, with the amino acid sequence SEQ ID NO: 2.

In an especial embodiment, the invention relates to a peptide comprising or consisting of sequence SEQ ID NO: 2.

In an especial embodiment, said peptide sequence SEQ ID NO: 2 is an isolated and/or purified peptide, a synthetic peptide, or a recombinant peptide.

In another aspect, the invention relates to a composition, especially a phytosanitary composition, comprising the miPEP172c as active substance, said miPEP172c consisting preferably of SEQ ID NO: 2.

In another aspect, the invention relates to a peptide having an amino acid sequence having at least 80% identity, preferably at least 90% identity, with the amino acid sequence SEQ ID NO: 7.

In an especial embodiment, the invention relates to a peptide comprising or consisting of sequence SEQ ID NO: 7.

In an especial embodiment, said peptide sequence SEQ ID NO: 7 is an isolated and/or purified peptide, a synthetic peptide, or a recombinant peptide.

In one embodiment, the invention relates to a peptide as defined above, said peptide being labelled.

In a non-limiting manner, a labelled peptide can be obtained especially by fusing said peptide to another peptide sequence, to a fluorescent marker (GUS, GFP, LacZ, etc.), to a signal sequence (making it possible to address the peptide), to a Tag sequence (making it possible to purify the miPEP), or to a radioactive isotope.

In the case in which the peptide of the invention is labelled with the aid of another peptide sequence, this is not taken into consideration to calculate a percentage of identity compared to the peptide of the invention.

In another aspect, the invention relates to a composition, especially a phytosanitary composition, comprising the miPEP167c as active substance, said miPEP167c preferably consisting of SEQ ID NO: 7.

In another aspect, the invention relates to a composition as defined above in which said miPEP172c is at a concentration of from $10^{-9}$M to $10^{-4}$M, especially $10^{-9}$, $10^{-8}$, $10^{-7}$, $10^{-6}$, $10^{-5}$ or $10^{-4}$ M.

Preferably, a composition as defined above has a concentration of from $10^{-8}$ M to $10^{-5}$M for application by watering or by spraying onto the plant, or by addition of a fertiliser, a soil, a culture substrate, or with the aid of a support in contact with the plant.

Preferably, a composition as defined above has a concentration of from $10^{-8}$ M to $10^{-5}$M for application by watering or by spraying onto the plant, or by addition of a fertiliser, a soil, a culture substrate, or with the aid of a support in contact with the grain or seed.

In a complementary manner, compositions that are concentrated to a greater or lesser extent can be envisaged to treat the plant with the miPEP. For example, and in a non-limiting manner, compositions concentrated to a greater extent comprising from $10^{-1}$ M to $10^{-3}$ M, especially $10^{-2}$ M of miPEP, can be used in the case in which the miPEP introduced exogenously is administered to the plant by spreading.

In another aspect, the invention relates to a composition as defined above, further comprising an excipient, a diluent, or a solvent.

In one embodiment, the invention relates to a composition as defined above, formulated so as to form a coated product.

In one embodiment, the invention relates to a composition as defined above:
in the form of a granule,
formulated so as to form a granule, or
formulated so as to be contained in a granule.

In another aspect, the invention relates to a composition comprising, in combination, a quantity of seeds of a plant and a quantity of a peptide of which the sequence comprises or consists of a sequence identical to that of a miPEP naturally present in said plant.

In one embodiment, the invention relates to a composition comprising, in combination, a quantity of seeds of a plant, especially *Glycine max*, and a quantity of a peptide of which the sequence comprises or consists of a sequence identical to that of miPEP172c.

In one embodiment, the invention relates to a composition comprising, in combination, a quantity of seeds of a plant, especially *Glycine max*, and a quantity of a peptide of which the sequence comprises or consists of a sequence identical to that of miPEP167c.

In another aspect, the invention relates to a composition as defined above, further comprising an excipient, a diluent, or a solvent.

In one embodiment, the invention relates to a composition as defined above, formulated so as to form a coated seed or a coated grain.

The coating can be provided in accordance with the methods used conventionally in the agri-food industry and can be obtained using a material able to disintegrate in a solvent or in the ground, such as a binder or clay.

The composition containing said miPEP especially can be applied to the seed, beneath, in, or on the coating layer.

In accordance with the invention, the coating can be used for example to provide particular properties to a miPEP composition, or to a composition of seeds in combination with a miPEP.

In another aspect, the invention relates to a seed coated with a composition comprising a miPEP capable of modulating the accumulation of a miR in the plant produced from the seed, which miR regulates the expression of at least one gene involved in the nodulation in said plant.

In one embodiment, the invention relates to a seed coated with a composition comprising miPEP172c.

In one embodiment, the invention relates to a seed coated with a composition comprising a peptide of which the sequence has at least 80% identity, preferably at least 90% identity, with the sequence SEQ ID NO: 2.

In one embodiment, the invention relates to a seed coated with a composition comprising the peptide SEQ ID NO: 2.

In one embodiment, the invention relates to a seed coated with a composition comprising miPEP167c.

In one embodiment, the invention relates to a seed coated with a composition comprising a peptide of which the sequence has at least 80% identity, preferably at least 90% identity, with the sequence SEQ ID NO: 7.

In one embodiment, the invention relates to a seed coated with a composition comprising the peptide SEQ ID NO: 7.

In one embodiment, the invention relates to a coated seed as defined above, said plant being a leguminous plant, such as lotus (*Lotus* sp.) soybean (*Glycine max*), peanut (*Arachis hypogaea*), common bean (*Phaseolus vulgaris*), pea (*Pisum sativum*), lentil (*Lens culinaris*), chickpea (*Cicer arietinum*), broad bean and field bean (*Vicia faba*), vetches (*Vicia* sp.), vetchlings (*Lathyrus* sp.), alfalfa (*Medicago* sp.), clover (*Trifolium* sp.), lupin (*Lupinus* sp.), mungo bean (*Vigna radiata*), liquorice (*Glycyrrhiza glabra*), rosewood (*Dalbergia*), trefoil (*Lotus corniculatus*), sainfoin (*Onobrychis viciifolia*), rooibos (*Aspalathus linearis*), or fenugreek (*Trigonella foenum-graecum*).

In another aspect, the invention relates to a protocol for production of a recombinant peptide, of which the sequence comprises or consists of a sequence identical to that of a miPEP as defined above, comprising a step of transformation of an organism with an expression vector coding said recombinant peptide.

In one embodiment, said organism is selected from the group comprising bacteria, yeasts, fungi (other than yeasts), animal cells, plants, and animals.

In one embodiment, said organism is *Escherichia coli*.

Especially, the invention relates to a protocol for production of a recombinant peptide as defined above, comprising the following steps:
- the nucleic acid coding said recombinant peptide is linked to a nucleic acid coding a marker, such as GST,
- the expression vector containing said nucleic acid coding said recombinant peptide is introduced into the *E. coli* bacterium,
- the *E. coli* bacterium containing the expression vector is cultivated in the medium LB, preferably to a DO between 0.2 and 0.4,
- the production of the recombinant peptide is induced with IPTG, preferably for 4 to 5 hours,
- the *E. coli* bacteria are centrifuged and lysed,
- the supernatant is filtered,
- said recombinant peptide is purified over a glutathione sepharose affinity column,
- if necessary, the GST is cleaved with a protease.

In another aspect, the invention relates to a bacterium transformed with a sequence coding a miPEP as defined above.

In one embodiment, the invention relates to a bacterium transformed with a sequence coding a miPEP, said bacterium being a bacterium from the Rhizobiaceae family.

In one embodiment, the invention relates to a bacterium transformed with a sequence coding a miPEP, said bacterium being selected from the genera *Rhizobium, Sinorhizobium, Mesorhizobium, Bradyrhizobium* or *Azorhizobium*.

In one embodiment, the invention relates to a bacterium transformed with a sequence coding a miPEP, said bacterium being selected from the genera *Rhizobium leguminosarum, Rhizobium etli, Rhizobium tropici, Rhizobium galegae, Sinorhizobium* sp. NGR234, *Sinorhizobium meliloti, Sinorhizobium fredii, Sinorhizobium saheli, Sinorhizobium teranga, Mesorhizobium ciceri, Mesorhizobium huakuii, Mesorhizobium loti, Bradyrhizobium elkanii, Bradyrhizobium japonicum, Bradyrhizobium lupini, Bradyrhizobium* sp. "cowpea" and *Azorhizobium caulinodans*.

In another aspect, the invention relates to an antibody recognising, specifically, miPEP172c, especially said miPEP172c consisting of SEQ ID NO: 2.

An antibody of this type can be obtained from a method known to a person skilled in the art, for example by injecting said miPEP172c into a non-human animal so as to trigger an immune response and antibody production by said animal.

In another aspect, the invention relates to a method of immunolocalisation of miPEP172c comprising a step of labelling a biological sample of a plant with an antibody recognising, specifically, said miPEP172c.

In another aspect, the invention relates to an antibody recognising, specifically, miPEP167c, especially said miPEP167c consisting of SEQ ID NO: 7.

An antibody of this type can be obtained from a method known to a person skilled in the art, for example by injecting said miPEP167c into a non-human animal so as to trigger an immune response and antibody production by said animal.

In another aspect, the invention relates to a method of immunolocalisation of miPEP167c comprising a step of labelling a biological sample of a plant with an antibody recognising, specifically, said miPEP167c.

In another aspect, the invention relates to a method for culturing bacteria, comprising a step of contacting said bacteria:
- with a mixture comprising a plant or a plant part, especially a root culture, and a peptide of which the sequence comprises or consists of a sequence identical to that of a miPEP naturally present in said plant, said naturally present miPEP being a peptide of which the sequence is coded by an open reading frame at the 5' portion of the primary transcript of a miR, said miPEP being capable of modulating the accumulation of said miR, which miR regulates the expression of at least one gene involved in the nodulation in said plant, or
- with a transgenic plant as defined above, the plant, the plant part, and the transgenic plant being able to form a symbiosis with said bacterium.

In an especial embodiment, the invention relates to the method as defined above in which the cultivated bacteria belong to the Rhizobiaceae family.

In an especial embodiment, the invention relates to the method as defined above in which said bacteria are selected from the genera *Rhizobium, Sinorhizobium, Mesorhizobium, Bradyrhizobium* or *Azorhizobium*.

In an especial embodiment, the invention relates to a method as defined above in which said bacteria are selected from *Rhizobium leguminosarum, Rhizobium etli, Rhizobium tropici, Rhizobium galegae, Sinorhizobium* sp. NGR234, *Sinorhizobium meliloti, Sinorhizobium fredii, Sinorhizobium saheli, Sinorhizobium teranga, Mesorhizobium ciceri, Mesorhizobium huakuii, Mesorhizobium loti, Bradyrhizobium elkanii, Bradyrhizobium japonicum, Bradyrhizobium lupini, Bradyrhizobium* sp. "cowpea" and *Azorhizobium caulinodans*.

Especially, the method for culturing said bacteria as defined above is performed in culture conditions allowing the growth or improvement of the growth of the plant, of the plant part, and of the transgenic plant, and of the bacteria.

Especially, the method for culturing bacteria as defined above is performed in culture conditions allowing symbiosis between the bacterium and the plant, the plant part, or the transgenic plant.

In one embodiment, the peptide present in the mixture is an isolated peptide, an isolated and/or purified peptide, a synthetic peptide, or a recombinant peptide.

In one embodiment, the invention relates to a method for culturing bacteria as defined above in which said miR is miR172c, especially in which said miR172c has a nucleotide sequence consisting of SEQ ID NO: 1.

In one embodiment, the invention relates to a method for culturing bacteria as defined above in which said miPEP is miPEP172c, especially in which said miPEP172c has an amino acid sequence consisting of SEQ ID NO: 2.

In one embodiment, the invention relates to a method for culturing bacteria as defined above in which said miR is miR167c, especially in which said miR167c has a nucleotide sequence consisting of SEQ ID NO: 6.

In one embodiment, the invention relates to a method for culturing bacteria as defined above in which said miPEP is miPEP167c, especially in which said miPEP167c has an amino acid sequence consisting of SEQ ID NO: 7.

Especially, the invention relates to a method for culturing bacteria as defined above in which said plant part is a root or root fragment.

In another aspect, the invention relates to a method for producing a bacterial inoculum, especially of bacteria from the Rhizobiaceae family, comprising:

a step of co-culturing bacteria with a living plant matter, referred to as the host plant, corresponding at least in part to a constituent part of the root of a plant able to form a symbiosis with said bacteria, and a step of contacting a quantity of a peptide with the aforesaid co-culture, said peptide having a sequence comprising or consisting of a sequence identical to that of a miPEP naturally present in said host plant, said naturally present miPEP being a peptide of which the sequence is coded by an open reading frame at the 5' portion of the primary transcript of a miR, said miPEP being capable of modulating the accumulation of said miR, which miR regulates the expression of at least one gene involved in the nodulation in said host plant.

The invention also relates to a method for producing a bacterial inoculum, especially of bacteria from the Rhizobiaceae family, comprising a step of co-culturing bacteria with a living plant matter, referred to as a host plant, corresponding at least in part to a constituent part of the root of a plant able to form a symbiosis with said bacteria, and said host plant being a transgenic plant or a plant into which a peptide has been introduced, said peptide having a sequence comprising or consisting of a sequence identical to that of a miPEP naturally present in said host plant, said naturally present miPEP being a peptide of which the sequence is coded by an open reading frame at the 5' portion of the primary transcript of a miR, said miPEP being capable of modulating the accumulation of said miR, which miR regulates the expression of at least one gene involved in the nodulation in said host plant.

The invention also relates to a method for producing a bacterial inoculum, especially of bacteria from the Rhizobiaceae family, comprising a step of mixing together:

bacteria, a living plant matter, referred to as a host plant, corresponding at least in part to a constituent part of the root of a plant able to form a symbiosis with said bacteria, and a peptide, said peptide having a sequence comprising or consisting of a sequence identical to that of a miPEP naturally present in said host plant, said naturally present miPEP being a peptide of which the sequence is coded by an open reading frame at the 5' portion of the primary transcript of a miR, said miPEP being capable of modulating the accumulation of said miR, which miR regulates the expression of at least one gene involved in the nodulation in said host plant.

In another aspect, the invention relates to a bacterial inoculum, especially an inoculum of bacteria from the Rhizobiaceae family, suitable for the inoculation of a host plant, comprising at least one bacterium and a peptide of which the sequence comprises or consists of a sequence identical to that of a miPEP naturally present in the host plant, said miPEP naturally present in the host plant being a peptide of which the sequence is coded by an open reading frame at the 5' portion of the primary transcript of a miR, said miPEP being capable of modulating the accumulation of said miR, which miR regulates the expression of at least one gene involved in the nodulation in said host plant.

Preferably, said miPEP is miPEP172c.

Preferably, said miPEP is miPEP167c.

The peptide used to produce the inoculum, or the peptide present in the inoculum, is especially an isolated peptide, an isolated and/or purified peptide, a synthetic peptide, or a recombinant peptide.

The inoculum preferably additionally contains a plant or a plant part, especially a root, a root culture, or a root part.

The sequences of miPEP172c, of its open reading frame, of miR172c, and of the primary transcript of miR172c in *Glycine max* are indicated in table 1.

TABLE 1

| | | |
|---|---|---|
| miR172c | GGAAUCUUGAUGAUGCUGCAG | SEQ ID NO: 1 |
| miPEP172c | MWVLCLFCWPTYTHGS | SEQ ID NO: 2 |
| miORF172c | ATGTGGGTCTTGTGTTTGTTTGTTGGCCTA CATATACACATGGGAGTTGA | SEQ ID NO: 3 |
| pri-miR172c | CACTCTCTCATCTCTACTTGACCACTCTCTC TATATATACACCACTAAACCCTTTCTTCGTT CTCAGTTATCTTCTTTCACTTCACTTAACCT AGCCTCCTTCCCATTCTGATTTGAGTTCTTG CTTTGCCTCTTAATTTTATTTTTCCTCTTAGC TTTCTTCGATCTTAACCTTTGAACAGTAATT GCTTGCTTTGTATACATTAATTACTATAGGT GGTACTTTGGCAGCTTTTCTATTGTATAGAG ACTTATCAGTGAATAATACTACTATGTGGGT CTTGTGTTTGTTTTGTTGGCCTACATATACA CATGGGAGTTGAGGAGCCTTTTAGGCCTTA GCCTTACATTAGTTGTCCCTCTTTCCTTGCCT TTACTTTTGCTTCATATATTGGATTTGATTA GATTTAGGGTTAGGGTTAGGGCTGTTCTATT CTCCTCCTCCTCCTTTTCTACTTCCTGATATG CTTCAATTCCTCCTCTCTCTCTCTCTCTCTTG AAGTTTTATGTTTTATGGCCAAGTGATCTTA ATGGTGGTAACACAGAGAGACCTAATGAAG TCCTAAATAAACTAAAGAAATCAGTCACTG TTTGCCGGTGGAGCATCATCAAGATTCACA AGCTTTAGGGGCATTAATTTGTTTGAGGTGG TTCCTTATTGCTCCAAAACCAATTAGCCCTT TTGCTATGGGAATCTTGATGATGCTGCAGC | SEQ ID NO: 4 |

TABLE 1-continued

```
AGCAATAAATGACTAATACTACTACCAGAT
ATTGCTTGAGGAGGATCTCACTACTACACA
ACTGTGCTACAAGGCCAGGAGCAAAGGAG
GTTATTTAATTAACTAAATAATTATGTTATT
AATTTGTTTTCTAAATATTCAAGAAATTGGA
TTAGGTAATTACCAAGTTACAAGCCACTTTT
GGATTTACCTTTATTAACTCTAGTAGCTGAT
AAAT
```

The sequences of miPEP167c, of its open reading frame, of miR167c, and of the primary transcript of miR167c in *Glycine max* are indicated in table 2.

TABLE 2

| miR167c | UGAAGCUGCCAGCAUGAUCUG | SEQ ID NO: 6 |
|---|---|---|
| miPEP167c | MKGVHHFFHHKYVGLRG | SEQ ID NO: 7 |
| miORF167c | ATGAAAGGGGTTCATCACTTTTTTCATCACA AGTATGTTGGTTTGAGAGGT | SEQ ID NO: 8 |
| pri-miR167c | GAAAAGGAAGTCATTGTCAATAGCTGTAAG GAGGAGCAAAACCTACCATTAAATACTCCC TCTATGGCACAGTAGTGAAAGAAAAGAGAC ATTGAGCTGCGCACAGGCATTCATTCATAT GGATCAGTGTGGAGATAAAGAGGATCACGA GGGTCTCCCTTTAATTACTCCAAACATGCAT GGCTTGTTCCCCTTTTTGTTAATTTCTATGTA TCAAGATGTTGGTACCCTCTCTCAGGATTTG CTTCAATGAAAGGGGTTCATCACTTTTTTCA TCACAAGTATGTTGGTTTGAGAGGTTGAAG CTGCCAGCATGATCTGGTAAATCACATACTT TTTTTTTTCTCACCTCTCATGCCTAATTTTTA AGCACCAGTCATTAGAGAAAATAATGGTGA AAAATCCATCTATTCAATTTTTTTTTCAAA TTCAAGGTTTCCAGTATGTATCACTAATGGT GAAAAAAGTGATGGAATTTTGTAGAACATG GGTTAAATTTACTTTTTTTTTTTTGAGTTTT CATTTTCTTCAAGTTTCTGAGCCAAGAAATA AAAGAGACTTATAAATTGGAATTAATACTT AAAGGAAACCCACCAGAAGGGCAATTTGGT TATCATAAGATGTGGTTTCCATCAGGTCATC TTGCAGCTTCAATCACTCAAT | SEQ ID NO: 9 |

Pages 36 to 48 correspond to extracts from French patent application no. FR 13/60727 filed on 31 Oct. 2013 for "Micropeptides and use thereof for modulating gene expression"

Extracts from Application FR 13 60727

Application FR 13 60727 relates to micropeptides (peptides coded by microRNAs or "miPEPs") and use thereof for modulating gene expression.

MicroRNAs (miRs) are small non-coding RNAs, about 21 nucleotides in length after maturation, which control expression of target genes at the post-transcriptional level, by degrading the target mRNA or by inhibiting its translation. The miRs occur in plants and animals.

The target genes are often key genes in developmental processes. For example they code transcription factors or proteins of the proteasome.

The regulation of the expression of miRs is very poorly understood, but it has been found that it involves, like most coding genes, an RNA polymerase II: this enzyme produces a primary transcript, referred to as "pri-miR", which is then matured by a protein complex containing Dicer-type enzymes especially. This maturation leads firstly to the formation of a miR precursor referred to as a "pre-miR", having a stem-loop secondary structure containing the miR and its complementary sequence miR*. The precursor is then matured, which leads to the formation of a shorter double-stranded RNA containing the miR and the miR*. The miR is then manipulated by the RISC complex, which cleaves the mRNA from the target gene or inhibits the translation thereof.

Moreover, it has been shown that the presence of introns in the primary transcript of the microRNA increases the expression of the mature microRNA (Schwab et al., EMBO Rep., 14(7): 615-21, 2013). However, owing to experimental difficulties, the primary transcripts of microRNAs, or pri-miRs, have received very little study.

About 50% of eukaryotic genes have small open reading frames within their 5'UTR region (5' UnTranslated Region) upstream of the coding sequence. These small open reading frames (or "uORFs" for upstream ORFs) may perform a role of translation regulator, mainly in cis, by modulating the fixation and the rate of the ribosomes on the mRNA, but also in trans by an as yet unknown mechanism, by means of peptides coded by said uORFs (Combier et al., Gene Dev, 22: 1549-1559, 2008). By definition, the uORFS are present upstream of coding genes.

Recently, small ORFs have also been discovered in long intergenic non-coding RNAs (lincRNAs), the putative function of which, if it exists, is not known (Ingolia et al., Cell, 147(4): 789-802, 2011; Guttman & Rinn, Nature, 482 (7385): 339-46, 2012).

However, no example has yet been reported concerning the existence of ORFs encoding peptides within non-coding microRNAs. Until now, the microRNAs, and by extension their primary transcript, have always been regarded, based on their particular mode of action, as non-coding regulatory RNAs that do not produce any peptide.

One of the aspects of application FR 13 60727 is to propose peptides capable of modulating the expression of microRNAs.

Another aspect of application FR 13 60727 is to propose a means for modulating the expression of one or more target genes of a microRNA.

Application FR 13 60727 offers the advantage of allowing easier and more effective control of the expression of genes targeted by the microRNAs, through a means other than the microRNA.

Application FR 13 60727 thus relates to a method for detecting and identifying a micropeptide (miPEP) coded by a nucleotide sequence contained in the sequence of the primary transcript of a microRNA, comprising
 a) a step of detecting an open reading frame from 15 to 303 nucleotides in length contained in the sequence of the primary transcript of said microRNA, then
 b) a step of comparison between:
  the accumulation of said microRNA in a specified eukaryotic cell expressing said microRNA,
  in the presence of a peptide coded by a nucleotide sequence that is identical or degenerate relative to that of said open reading frame, said peptide being present in the cell independently of transcription of the primary transcript of said microRNA, and
  the accumulation of said microRNA in a eukaryotic cell of the same type as the aforesaid specified eukaryotic cell expressing said microRNA, in the absence of said peptide,
 in which a modulation of the accumulation of said microRNA in the presence of said peptide relative to the accumulation of said microRNA in the absence of said peptide indicates the existence of a micropeptide coded by said open reading frame.

In a first step, the method for detecting and identifying a micropeptide therefore consists of detecting, on the primary transcript of a microRNA, the existence of an open reading frame potentially encoding a peptide.

For its part, the second step makes it possible to characterise said peptide, i.e. to determine whether said peptide corresponds to a peptide really produced in the cell, by searching for an effect of said peptide on the accumulation of said microRNA.

In order to demonstrate an effect of the peptide on the accumulation of the microRNA, a large quantity of peptide is introduced into a first cell expressing said microRNA. The accumulation of the microRNA in this first cell is then measured and compared with the accumulation of the microRNA in a second cell identical to the first, but not containing said peptide.

Observation of a variation of the quantities of microRNA between the cells in the presence and in the absence of the peptide thus indicates (i) that there is a peptide coded on the primary transcript of said microRNA, (ii) that the sequence of this peptide is coded by the open reading frame identified on the primary transcript of said microRNA, and (iii) that said peptide has an effect on the accumulation of said microRNA.

Application FR 13 60727 is therefore based on the unexpected double observation made by the inventors that, on the one hand, there are open reading frames that are able to code micropeptides present on the primary transcripts of microRNAs, and on the other hand that said micropeptides are capable of modulating the accumulation of said microRNAs.

In application FR 13 60727, the terms "microRNA", "non-coding microRNA" and "miR" are equivalent and may be used interchangeably. They define small molecules of RNA of about 21 nucleotides, which are not translated and do not lead to a peptide or a protein.

However, in this mature form, the microRNAs perform a function of regulation of certain genes via post-transcriptional mechanisms, for example by means of the RISC complex.

The primary transcript of the microRNA or "pri-miR" corresponds to the RNA molecule obtained directly from transcription of the DNA molecule. Generally, this primary transcript undergoes one or more post-transcriptional modifications, involving for example an especial structure of the RNA or cleavage of certain portions of the RNA by splicing phenomena, and which lead to the precursor form of the microRNA or "pre-miR", then to the mature form of the microRNA or "miR".

The terms "micropeptides" and "miPEPs" (microRNA coded PEPtides) are equivalent and may be used interchangeably. They define a peptide that is coded by an open reading frame present on the primary transcript of a microRNA, and which is capable of modulating the accumulation of said microRNA. The micropeptides within the meaning of application FR 13 60727 are not to be understood as necessarily being small peptides, as "micro" does not correspond to the size of the peptide.

Taking into account the degeneracy of the genetic code, one and the same micropeptide is or may be coded by several nucleotide sequences. Nucleotide sequences of this kind, differing from one another by at least one nucleotide but encoding one and the same peptide, are called "degenerate sequences".

The terms "open reading frame" or "ORF" are equivalent and may be used interchangeably. They correspond to a nucleotide sequence in a DNA or RNA molecule that may potentially code a peptide or a protein: said open reading frame begins with a start codon, followed by a series of codons, and ends with a stop codon).

In application FR 13 60727, the ORFs may be called specifically "miORFs" when they are present on the primary transcripts of microRNA.

In application FR 13 60727, "accumulation" means the production of a molecule, such as a microRNA or a micropeptide, in the cell.

Thus, the "modulation" of the accumulation of a molecule in a cell corresponds to a modification of the quantity of this molecule present in the cell.

In one embodiment, application FR 13 60727 relates to a method for detecting and identifying a miPEP as defined above in which the modulation of the accumulation of said microRNA is a decrease or an increase in the accumulation of said microRNA, especially an increase.

A "decrease in the accumulation" corresponds to a decrease in the quantity of said molecule in the cell.

Conversely, an "increase in the accumulation" corresponds to an increase in the quantity of said molecule in the cell.

In an advantageous embodiment, application FR 13 60727 relates to a method for detecting and identifying a miPEP as defined above in which the modulation of the accumulation of said microRNA is an increase in the accumulation of said microRNA.

In one embodiment, application FR 13 60727 relates to a method for detecting and identifying a miPEP as defined above in which the presence of said peptide in the cell results from
- the introduction of a nucleic acid encoding said peptide into the cell, or
- the introduction of said peptide into the cell.

In order to characterise a miPEP, it is necessary to have a cellular model expressing a microRNA in which said peptide to be tested is present. For this, it is possible to introduce a peptide into the cell, either by bringing the cell into contact with said peptide, or by introducing a nucleic acid encoding said peptide into the cell, which nucleic acid will then be translated into peptide within the cell.

In one embodiment, application FR 13 60727 relates to a method for detecting and identifying a miPEP as defined above in which said open reading frame in step a) is contained in the 5' or 3' portion of said primary transcript of the microRNA, preferably in the 5' portion.

The 5' or 3' portions of the primary transcript of the microRNA correspond to the terminal portions of the RNA molecule that are cleaved during maturation of the microRNA.

In one embodiment, application FR 13 60727 relates to a method for detecting and identifying a miPEP as defined above in which said microRNA is present in a wild-type plant cell.

In application FR 13 60727, a wild-type plant cell corresponds to a plant cell that has not been genetically modified by humans.

In one embodiment, application FR 13 60727 relates to a method for detecting and identifying a miPEP as defined above in which said specified eukaryotic cell and said eukaryotic cell of the same type as the aforesaid specified eukaryotic cell, used in step b, are plant cells, preferably cells of *Medicago truncatula* or of *Arabidopsis thaliana*.

In the method for detecting and identifying a micropeptide as defined above, after identifying an ORF that is able to code a peptide on the primary transcript of a microRNA, it is necessary to have a cellular model having said microRNA and said peptide, so as to be able to demonstrate a possible effect of the peptide on said microRNA.

Two options are therefore conceivable:
- the cellular model in which the miORF has been identified and that in which the effect of the peptide on the miR has been demonstrated are identical, or
- the cellular model in which the miORF has been identified and that in which the effect of the peptide on the miR has been demonstrated are different.

In the first option, the cellular model used for observing an effect of the peptide is the same as that in which the primary transcript of said microRNA was isolated. In this cellular model, the specified eukaryotic cells contain said microRNA naturally and only the peptide to be tested has to be introduced into these cells. In this context, said microRNA is qualified as "of endogenous origin" as it exists naturally in the cells. Nevertheless, other copies of a microRNA of endogenous origin may be added to a cell, for example by introducing a vector encoding said microRNA of endogenous origin into the cell.

In the second option, the cellular model used for observing an effect of the peptide is different from that in which the primary transcript of said microRNA was isolated. In this cellular model, the specified eukaryotic cells contain neither the microRNA, nor the peptide to be tested. These two elements must therefore be introduced into these cells. In this context, said microRNA is qualified as "of exogenous origin" as it does not exist naturally in the cells.

In one embodiment, application FR 13 60727 relates to a method for detecting and identifying a miPEP as defined above in which said microRNA is of endogenous origin in said eukaryotic cell and in said eukaryotic cell of the same type as the aforesaid specified eukaryotic cell, used in step b).

In one embodiment, application FR 13 60727 relates to a method for detecting and identifying a miPEP as defined above in which said microRNA is of exogenous origin in said eukaryotic cell and in said eukaryotic cell of the same type as the aforesaid specified eukaryotic cell, used in step b), said eukaryotic cells containing a vector allowing the expression of said microRNA.

In one embodiment, application FR 13 60727 relates to a method for detecting and identifying a miPEP as defined above in which the accumulation of said microRNA is determined using quantitative RT-PCR or Northern blot.

In one embodiment, application FR 13 60727 relates to a method for detecting and identifying a miPEP as defined above in which the accumulation of said microRNA is determined using a DNA or RNA chip.

The accumulation of said microRNA may be determined using the techniques of molecular biology for assaying specific nucleic acid molecules.

In another aspect, application FR 13 60727 also relates to a method for detecting and identifying a microRNA in which the sequence of the primary transcript contains a nucleotide sequence encoding a miPEP, comprising:
a) a step of detecting an open reading frame from 15 to 303 nucleotides in length contained in the sequence of the primary transcript of said microRNA, then
b) a step of comparison between:
- the accumulation of said microRNA in a specified eukaryotic cell expressing said microRNA, in the presence of a peptide coded by a nucleotide sequence that is identical or degenerate relative to that of said open reading frame, said peptide being present in the cell independently of transcription of the primary transcript of said microRNA, and
- the accumulation of said microRNA in a eukaryotic cell, of the same type as the aforesaid specified eukaryotic cell expressing said microRNA, in the absence of said peptide, in which a modulation of the accumulation of said microRNA in the presence of said peptide relative to the accumulation of said microRNA in the absence of said peptide indicates the existence of a microRNA of which the primary transcript contains a nucleotide sequence encoding a micropeptide.

In one embodiment, application FR 13 60727 relates to a method for detecting and identifying a microRNA as defined above in which the modulation of the accumulation of said microRNA is a decrease or an increase in the accumulation of said microRNA, especially an increase.

In one embodiment, application FR 13 60727 relates to a method for detecting and identifying a microRNA as defined above in which the presence of said peptide in the cell results from:
- the introduction of a nucleic acid encoding said peptide into the cell, or
- the introduction of said peptide into the cell.

In one embodiment, application FR 13 60727 relates to a method for detecting and identifying a microRNA as defined above in which said open reading frame in step a) is contained in the 5' or 3' portion of said primary transcript of the microRNA, preferably in the 5' portion.

In one embodiment, application FR 13 60727 relates to a method for detecting and identifying a microRNA as defined above in which said microRNA is present in a wild-type plant cell.

In one embodiment, application FR 13 60727 relates to a method for detecting and identifying a microRNA as defined above in which said eukaryotic cell, and said eukaryotic cell of the same type as the aforesaid specified eukaryotic cell, used in step b) are plant cells, preferably cells of *Medicago truncatula*.

In one embodiment, application FR 13 60727 relates to a method for detecting and identifying a microRNA as defined above in which said microRNA is of endogenous origin in said eukaryotic cell and in said eukaryotic cell of the same type as the aforesaid specified eukaryotic cell, used in step b).

In one embodiment, application FR 13 60727 relates to a method for detecting and identifying a microRNA as defined above in which said microRNA is of exogenous origin in said eukaryotic cell and in said eukaryotic cell of the same type as the aforesaid specified eukaryotic cell, used in step b), said eukaryotic cells containing a vector allowing the expression of said microRNA.

In one embodiment, application FR 13 60727 relates to a method for detecting and identifying a microRNA as defined above in which the accumulation of said microRNA is determined using quantitative RT-PCR or Northern blot.

In one embodiment, application FR 13 60727 relates to a method for detecting and identifying a microRNA as defined above in which the accumulation of said microRNA is determined using a DNA or RNA chip.

In another aspect, application FR 13 60727 relates to a miPEP as obtained by implementing the method as defined above.

Another aspect of application FR 13 60727 also relates to a miPEP of 4 to 100 amino acids, preferably of 4 to 40 amino acids, coded by a nucleotide sequence contained in the primary transcript of a microRNA, said miPEP being capable of modulating the accumulation of said microRNA in a eukaryotic cell.

Moreover, it should be noted that several miORFS may be identified on the primary transcript of a microRNA, indicating that a primary transcript of microRNA may potentially code several miPEPs.

It should also be noted that the effect of a miPEP is generally specific to a single microRNA, namely that resulting from the primary transcript encoding said miPEP.

In one embodiment, application FR 13 60727 relates to a miPEP as defined above, said nucleotide sequence being contained in the 5' or 3' portion of said primary transcript of a microRNA, preferably in the 5' portion.

In one embodiment, application FR 13 60727 relates to a miPEP as defined above, said nucleotide sequence corresponding to the first open reading frame present on said primary transcript of a microRNA.

In one embodiment, application FR 13 60727 relates to a miPEP as defined above, said miPEP having a basic isoelectric point, preferably above 8.

In another aspect, application FR 13 60727 relates to a nucleic acid molecule encoding a miPEP as defined above.

In another aspect, application FR 13 60727 relates to a vector comprising at least one nucleic acid molecule as defined above.

In another aspect, application FR 13 60727 also relates to the use of at least:
one miPEP as defined above,
one nucleic acid encoding said miPEP, or
one vector containing said nucleic acid,
for modulating the expression of at least one gene in a specified eukaryotic cell, said specified eukaryotic cell being capable of expressing a microRNA, of which the primary transcript contains at least one nucleotide sequence encoding said at least one miPEP and the accumulation of which is modulated by said at least one miPEP, the expression of said at least one gene being regulated by said microRNA.

In another aspect, application FR 13 60727 also relates to the use of at least:
one miPEP of 4 to 100 amino acids, preferably of 4 to 40 amino acids, coded by a nucleotide sequence contained in the primary transcript of a microRNA, said miPEP being capable of modulating the accumulation of said microRNA in a eukaryotic cell,
one nucleic acid encoding said miPEP, or
one vector containing said nucleic acid,
for modulating the expression of at least one gene in a specified eukaryotic cell, said specified eukaryotic cell being capable of expressing a microRNA, of which the primary transcript contains at least one nucleotide sequence encoding said at least one miPEP and the accumulation of which is modulated by said at least one miPEP, the expression of said at least one gene being regulated by said microRNA.

Application FR 13 60727 is based on the surprising observation made by the inventors that it is possible to modulate the expression of one or more target genes of one and the same microRNA by modulating the accumulation of said microRNA using a miPEP.

In one embodiment, application FR 13 60727 relates to the use as defined above in which said specified eukaryotic cell is a plant cell.

In one embodiment, application FR 13 60727 relates to the use as defined above in which said microRNA and said gene are of endogenous origin in said specified eukaryotic cell.

In one embodiment, application FR 13 60727 relates to the use as defined above in which said microRNA and said gene are of exogenous origin in said specified eukaryotic cell, said specified eukaryotic cell containing at least one vector allowing the expression of said microRNA and of said gene.

In application FR 13 60727, the expressions "of endogenous origin" and "of exogenous origin" are used for distinguishing said microRNAs and/or the genes of different species, in view of the conservation of the sequences between species.

Thus, the term "of endogenous origin" indicates that the microRNA and/or gene may be present naturally in the cell in question. Other copies of the microRNA and/or of the gene of endogenous origin may nevertheless be added artificially to the cell in question, for example by cloning.

Conversely, the term "of exogenous origin" indicates that the microRNA and/or the gene are never present naturally in the cell in question. It is a microRNA and/or a gene identified in another cellular type or in an organism of another species; this microRNA and/or this gene are therefore necessarily introduced artificially into the cell in question.

In application FR 13 60727, a genetically transformed cell may therefore contain 2 groups of microRNAs and/or of genes potentially similar in terms of sequence, one of endogenous origin and the other of exogenous origin.

In another aspect, application FR 13 60727 relates especially to a method for modulating the expression of a gene regulated by a microRNA in a eukaryotic cell, comprising carrying out a step of accumulation of a miPEP in said eukaryotic cell,
    said miPEP having:
        a size from 4 to 100 amino acids, preferably 4 to 20 amino acids, and
        a peptide sequence identical to that coded by a nucleotide sequence contained in the primary transcript of a microRNA regulating the expression of said gene, and
        being capable of modulating the accumulation of said microRNA,
    in which the accumulation of said miPEP in said eukaryotic cell induces a modulation of the expression of said gene relative to the expression of said gene without accumulation of said miPEP.

In one embodiment, application FR 13 60727 relates to a method for modulating the expression of a gene as defined above in which the accumulation of said miPEP in the cell results from:
    introduction of a nucleic acid encoding said miPEP into the cell, or
    introduction of said miPEP into the cell.

In one embodiment, application FR 13 60727 relates to a method for modulating the expression of a gene as defined above in which said eukaryotic cell is a plant cell.

In one embodiment, application FR 13 60727 relates to a method for modulating the expression of a gene as defined above in which said microRNA and said gene are of endogenous origin in said eukaryotic cell.

In one embodiment, application FR 13 60727 relates to a method for modulating the expression of a gene as defined above in which said microRNA and said gene are of exogenous origin in said eukaryotic cell, said eukaryotic cell containing at least one vector allowing the expression of said microRNA and of said gene.

In another aspect, application FR 13 60727 relates to a modified eukaryotic cell containing a peptide identical to a miPEP as defined above, said peptide being present in said eukaryotic cell independently of transcription of the primary transcript of the microRNA bearing the nucleotide sequence encoding said miPEP In application FR 13 60727, the term "modified eukaryotic cell" means that said eukaryotic cell contains a miPEP introduced into the cell artificially, whether as a peptide, or via a vector encoding said miPEP.

In one embodiment, application FR 13 60727 relates to a modified eukaryotic cell as defined above in which said microRNA is of endogenous origin.

In another embodiment, application FR 13 60727 relates to a modified eukaryotic cell as defined above in which said microRNA is of exogenous origin, said modified eukaryotic cell containing a vector allowing the expression of said microRNA.

In one embodiment, application FR 13 60727 relates to a modified eukaryotic cell as defined above, said cell being a plant cell.

In another aspect, application FR 13 60727 relates to a plant comprising at least one modified eukaryotic cell as defined above.

In another aspect, application FR 13 60727 relates to a composition comprising at least:
    one miPEP as defined above,
    one nucleic acid encoding said miPEP, or
    one vector containing said nucleic acid.

In another aspect, application FR 13 60727 relates to a pesticide composition comprising at least:
    one miPEP as defined above,
    one nucleic acid encoding said miPEP, or
    one vector containing said nucleic acid.

In another aspect, application FR 13 60727 relates to a phytopharmaceutical composition comprising at least:
    one miPEP as defined above,
    one nucleic acid encoding said miPEP, or
    one vector containing said nucleic acid.

In another aspect, application FR 13 60727 relates to an elicitor composition comprising at least:
    one miPEP as defined above,
    one nucleic acid encoding said miPEP, or
    one vector containing said nucleic acid.

"Elicitor composition" denotes a composition capable of endowing the plant with better capacity for symbiosis or better resistance to different stresses, whether they are of the nature of thermal stress, water stress or chemical stress.

For this purpose, application FR 13 60727 also relates to compositions acting on the growth (inhibition of growth or conversely growth promotion) and the physiology (better capacity for mycorrhisation, nodule formation, better tolerance of different stresses) of the plant.

In another aspect, application FR 13 60727 relates to a herbicide composition comprising at least:
    one miPEP as defined above,
    one nucleic acid encoding said miPEP, or
    one vector containing said nucleic acid.

In another aspect, application FR 13 60727 relates to an insecticide composition comprising at least:
    one miPEP as defined above,
    one nucleic acid encoding said miPEP, or
    one vector containing said nucleic acid.

In another aspect, application FR 13 60727 relates to the use of a composition as defined above, as a herbicide for eliminating plants or speeding up the growth of plants, preferably as a herbicide specific to a plant species or genus.

In another aspect, application FR 13 60727 relates to the use of a composition as defined above, as a phytopharmaceutical agent,
    for promoting the growth and/or development of plants,
    especially for modulating the physiological parameters of a plant, especially the biomass, foliar surface area, flowering, fruit size, production and/or selection of plant seeds, especially for controlling the parthenocarpy or the monoecism of a plant, or for modifying the physiological parameters of plant seeds, especially germination, establishment of the root system and resistance to water stress,
    or for preventing or treating plant diseases,
    especially for promoting resistance to infectious diseases.

In another aspect, application FR 13 60727 relates to the use of a composition as defined above, for modulating the physiological parameters of a plant, especially biomass, foliar surface area, or fruit size.

In one embodiment, application FR 13 60727 relates to the use of a composition as defined above, for thinning of orchards in order to increase fruit size.

In one embodiment, application FR 13 60727 relates to the use of a composition as defined above, for production and/or selection of plant seeds, said composition being used for controlling the parthenocarpy or the monoecism of a plant.

In one embodiment, application FR 13 60727 relates to the use of a composition as defined above, said composition being administered to said plant via the leaves or via the roots.

In one embodiment, application FR 13 60727 relates to the use of a composition as defined above, for production and/or selection of plant seeds.

In one embodiment, application FR 13 60727 relates to the use of a composition as defined above in which said composition is used for modifying the physiological parameters of said plant seeds, especially establishment of the root system, germination and resistance to water stress.

In one embodiment, application FR 13 60727 relates to the use of a composition as defined above in which said composition is applied by coating or film-coating of said plant seeds.

In another aspect, application FR 13 60727 relates to the use of a composition as defined above, as a pesticide, for eradicating organisms that are harmful to plants or that might be classified as such, especially as insecticide, arachnicide, molluscicide or rodenticide.

In one embodiment, application FR 13 60727 relates to the use of a composition as defined above, as insecticide.

In one embodiment, application FR 13 60727 relates to the use of a composition as defined above, for eradicating insect pests.

In one embodiment, application FR 13 60727 relates to the use of a composition as defined above, for eradicating animal species classified as harmful or liable to be classified as such, especially the Muridae, especially the rat.

In another aspect, application FR 13 60727 relates to the use of a composition as defined above in which said composition is applied to a plant to protect it against insect pests.

The following drawings and examples will better illustrate the invention, without limiting the scope thereof.

KEY TO THE DRAWINGS

FIG. 1. Effects of a treatment with miPEP172c on the expression of miR172c in *Glycine max*

The ordinate axis indicates the relative expression of miR172c in a control plant (left column) or in a plant watered with miPEP172c at 0.1 µM (right column). The error bar corresponds to the standard error of the mean (number of individuals=9).

Figure 2:
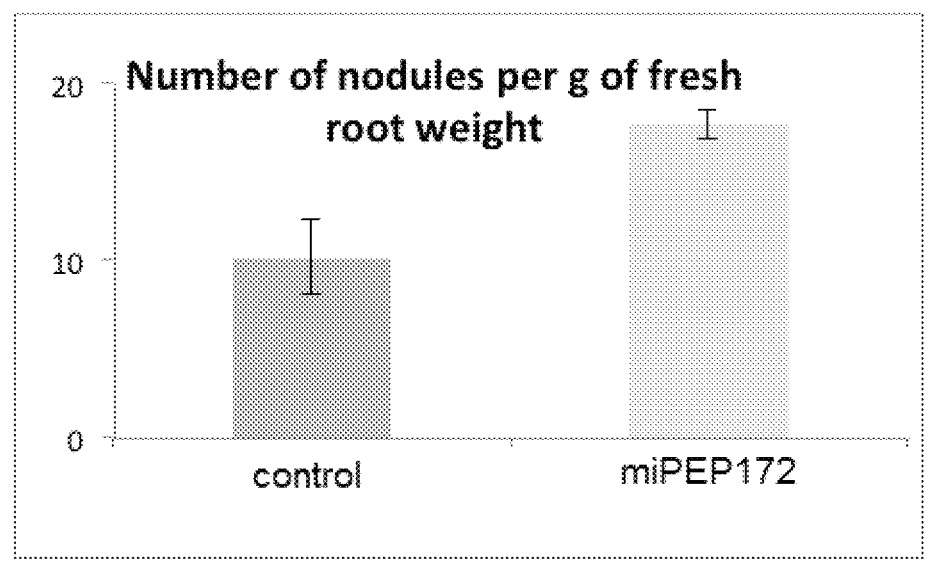

FIG. 2. Effects of miPEP172c on the number of nodules in *Glycine max*

The ordinate axis indicates the number of nodules per gram of fresh root weight of *Glycine max* treated with a solvent (control, left bar) or with a solvent containing 0.1 µM of miPEP172c (miPEP172c, right bar).

The error bar corresponds to the standard error of the mean (number of individuals=9).

This experiment was repeated independently and gave similar results.

Figure 3:
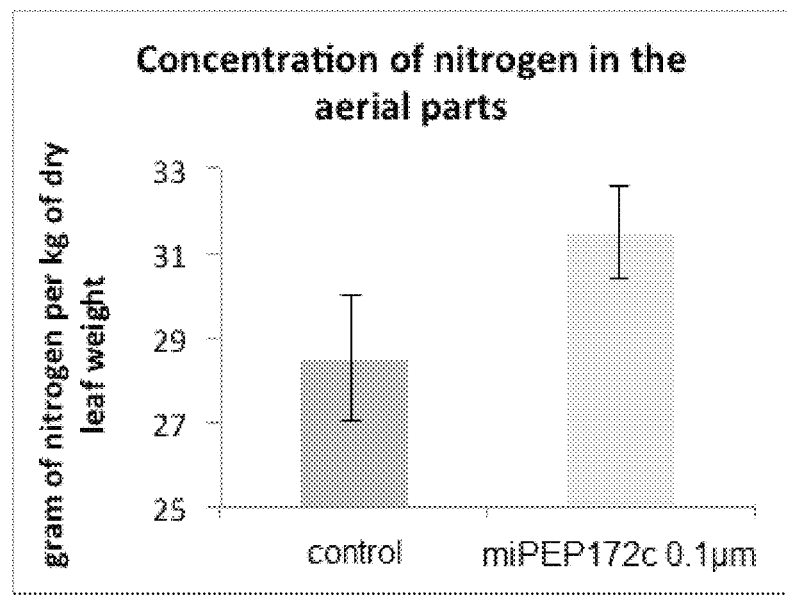

FIG. 3. Effects of miPEP172c on the nitrogen concentration in the aerial parts in *Glycine max*

The ordinate axis indicates the nitrogen concentration per dry leaf weight of *Glycine max* (in g/kg), treated with a solvent (control, left bar) or with a solvent containing 0.1 µM of miPEP172c (miPEP172c, right bar).

The error bar corresponds to the standard error of the mean (number of individuals=9).

Figure 4:
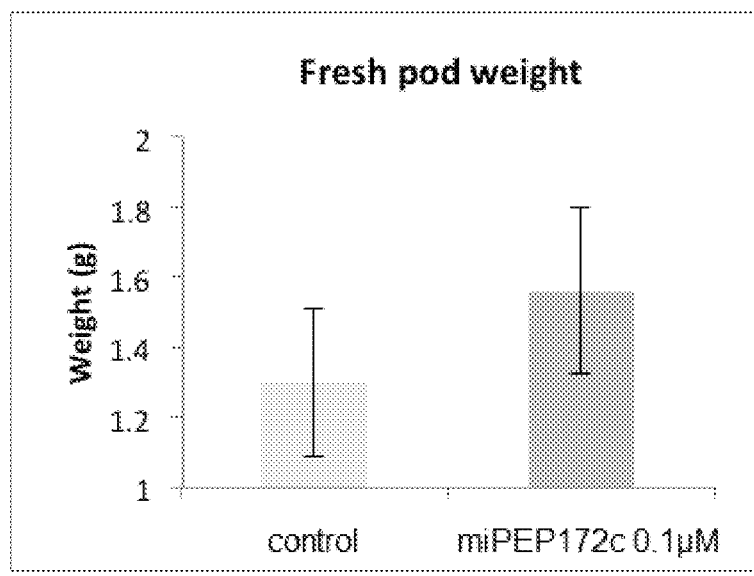

FIG. 4. Effects of miPEP172c on the fresh pod weight in *Glycine max*

The ordinate axis indicates the fresh dry pod weight in *Glycine max* (in g), treated with a solvent (control, left bar) or with a solvent containing 0.1 µM of miPEP172c (miPEP172c, 30 right bar).

The error bar corresponds to the standard error of the mean (number of individuals=9).

Figure 5:
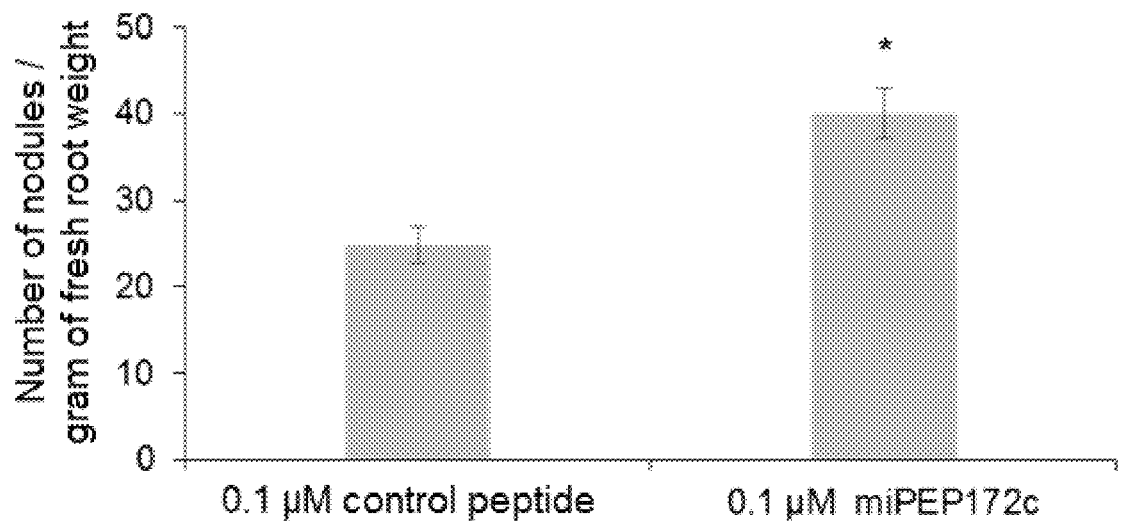

FIG. 5. Effects of miPEP172c on the number of nodules in *Glycine max*

The ordinate axis indicates the number of nodules per gram of fresh root weight of *Glycine max* treated with a solvent containing a control peptide at 0.01 µM (left bar) or with a solvent containing 0.1 µM of miPEP172c (right bar).

The error bar corresponds to the standard error of the mean (number of individuals=12).

The presence of an asterisk indicates a significant difference of expression between the two conditions tested.

Figure 6:
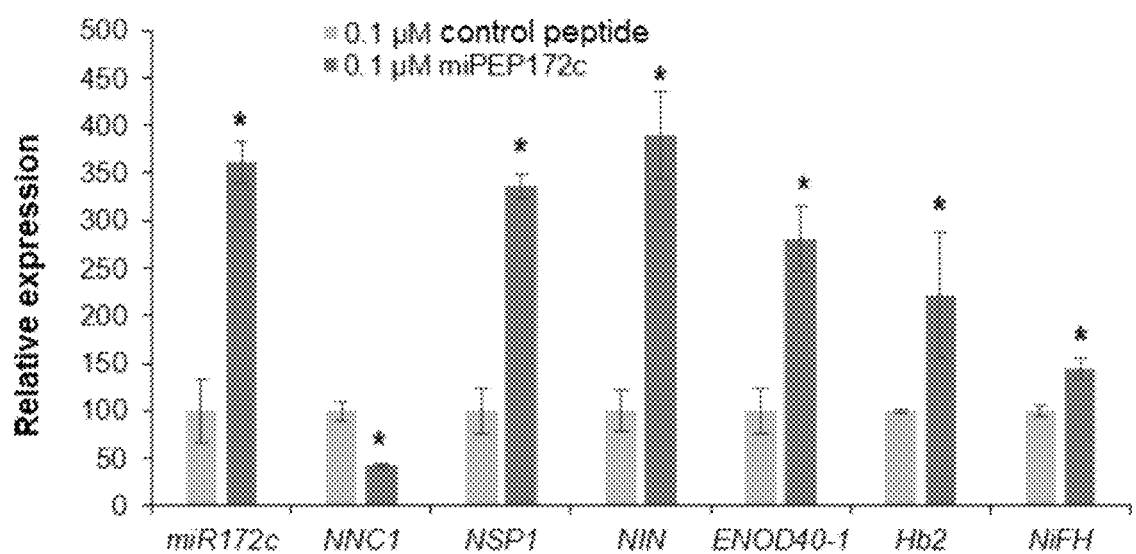

FIG. 6. Effects of miPEP172c on the expression of miR172c and on the expression of the genes NNC1, NSP1, NIN, ENOD40-1, Hb2 and nifH in *Glycine max*.

The ordinate axis indicates the relative expression of miR172c and of the genes NNC1, NSP1, NIN, ENOD40-1, Hb2 and nifH in a control plant watered with a solvent containing a control peptide at 0.01 µM (white columns) or in a plant watered with a solvent containing miPEP172c at 0.01 µM (black columns). The error bar corresponds to the standard error of the mean (number of individuals=6). The presence of an asterisk indicates a significant difference of expression between the two conditions tested.

Figure 7:
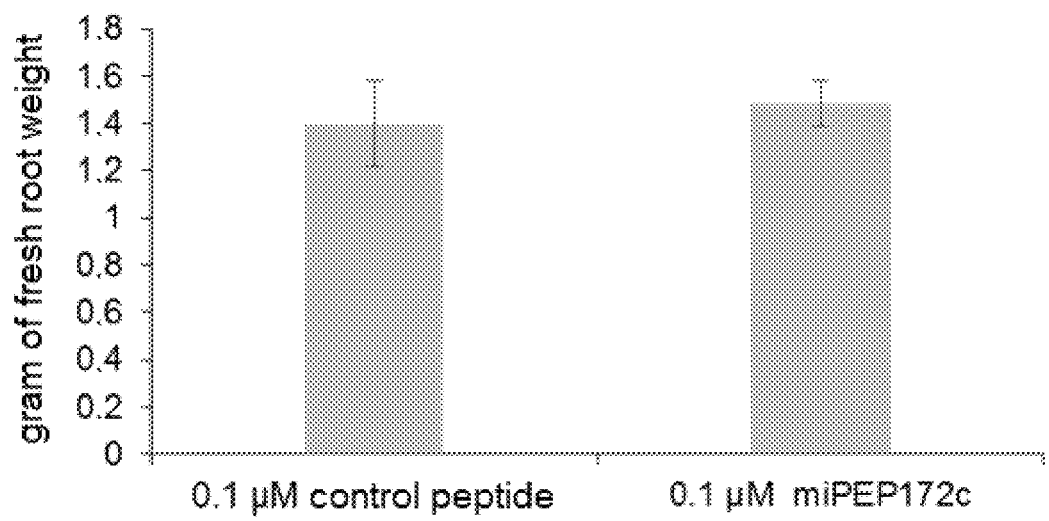

FIG. 7. Effects of miPEP172c on the root mass in *Glycine max*.

The ordinate axis indicates the fresh root weight in grams in a control plant watered with a solvent containing a control peptide at 0.01 µM (left column) or in a plant watered with a solvent containing miPEP172c at 0.01 µM (right column) (number of individuals=6).

Figure 8:
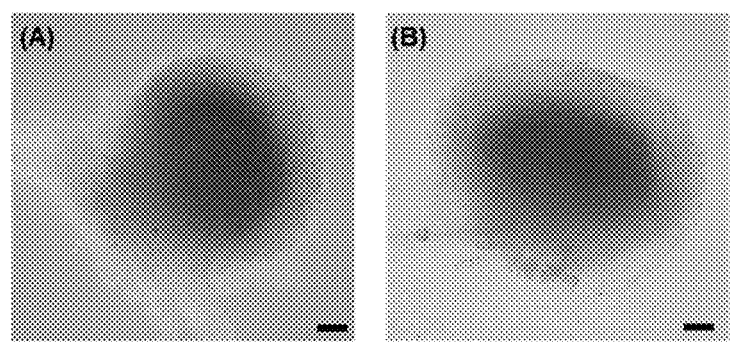

FIG. 8. Expression of the gene NifD.

The photographs show the expression of nifD revealed by nifD-LacZ fusions in nodules treated with the control peptide (A) or with miPEP172c (B).

Figure 9:
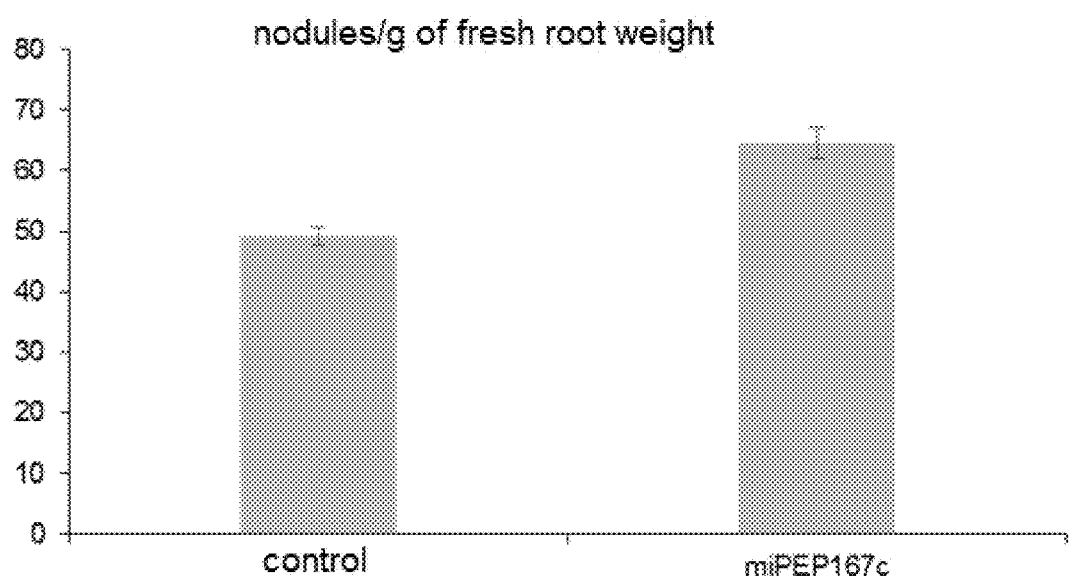

FIG. 9. Effects of miPEP167c on the number of nodules in *Glycine max* The ordinate axis indicates the number of nodules per gram of fresh root weight of *Glycine max* treated with a solvent (control, left bar) or with a solvent containing 0.1 µM of miPEP167c (miPEP167c, right bar).

The error bar corresponds to the standard error of the mean (number of individuals=12).

EXAMPLES

The miPEP172c increases the expression of miR172c (FIGS. 1 and 6). The effect of miPEP172c is agonistic to that of miR172c, reducing the expression of the gene NNC1 (repressive transcription factor) and prompting an increase in the expression of the genes NSP1, NIN, ENOD40-1, Hb2 and NifH involved in the nodulation (FIG. 6).

The watering of soybean plants (*Glycine max*) with low concentrations of miPEP172c (0.1 µM) specific to miR172c significantly increases the number of nodules (FIGS. 2 and 5) and the nitrogen content of the aerial parts (FIG. 3), as well as the fresh pod weight (FIG. 4). No effect on the development of the roots was observed (FIG. 7).

A rise in the number of inactive nodules sometimes occurs as a compensation mechanism in response to a reduced fixation of nitrogen. The analysis of the expression of the gene NifH by RT-qPCR (FIG. 6) and the observation of nifD::LacZ fusions (FIG. 8), however, indicate effective fixation of nitrogen in the plants treated with miPEP172c.

All of these results indicate that the treatment with miPEP172c mimics the effects of an overexpression of miR172c, both at molecular and phenotype level.

The watering of soybean plants (*Glycine max*) with low concentrations of miPEP167c (0.1 µM) specific to miR167c also significantly increases the number of nodules (FIG. 9).

Material and Methods

Measurement of the Expression of miR172c and of the Genes NNC1, NSP1, NIN and ENOD40-1 in *Glycine max*

The total RNA of the roots of soybean was extracted using the RNeasy Plant Mini Extraction Kit (Qiagen). The reverse transcription was performed using the reverse transcriptase SuperScript II (Invitrogen) from 500 ng of total RNA. Three repetitions (n=3) were performed with two technical repetitions each. Each experiment was repeated from two to three times. The amplifications by qPCR were performed using a LightCycler 480 Thermocycler System (Roche Diagnostics) in accordance with the method described in Lauressergues et al. (*Plant J.*, 72(3):512-22, 2012). ELF1b was used as housekeeping gene to standardise the qRT-PCR analyses. The primers used for the amplification of the genes ELF1b, NNC1, NSP1, NIN, ENOD40-1, Hb2 and nifH are described in the articles of Wang et al. (Soybean miR172c targets the repressive AP2 transcription factor NNC1 to activate ENOD40 expression and regulate nodule initiation, *Plant cell* 26(12): 4782-4801, 2014; MicroRNA167-directed regulation of the auxin response factors GmARF8a and GmARF8b is required for soybean nodulation and lateral root development, *Plant Physiol* 168(3): 984-999, 2015).

Germination of *G. max* Grains:

After sterilisation of the grains for 3 min in bleach diluted ¼, then rinsing with sterile water, the grains are incubated for 2 hours in water. Lastly, the grains are placed in a petri dish with damp paper towels at 28° C. Once sprouted, the grains are placed in a small pot containing Oil Dry® medium under a glass cover. After a few days' growth, the plants of which the development is uniform are selected for the experiment and transferred into a larger pot.

Inoculation of the Sprouted Seedlings with *Bradirhizobium japonicum*:

The bacteria are placed in culture in Campbel liquid medium ($K_2PO_4$: 0.5 g/l, $MgSO_4$ $7H_2O$: 0.2 g/l, NaCl: 0.1 g/l, mannitol: 10 g/l, yeast extract: 2.5 g/l, Casamino acid: 0.5 g/l) (5 ml) at 28° C., then transferred to an Erlenmeyer flask containing 100 ml of Campbel medium. After a few days of culture, when the DO is 0.3 at 595 nm, the 100 ml of culture of *B. japonicum* were centrifuged for 30 min at 4000 rpm. The supernatant was discarded and the pellet resuspended in "caisson" culture medium (Lullien et al., Plant gene expression in effective and ineffective root nodules of alfalfa (*Medicago sativa*). Plant Mol Biol 9: 469-478, 1987) to achieve a DO of 0.05 at 595 nm. Each plant is inoculated with 20 ml of this solution. The plants are regularly watered with the "caisson" medium.

Plant Treatments with the miPEPs:

The treatment is performed by watering plants with the concentrated solution of miPEP or the equivalent of solvent solution for the control treatment. A control treatment is also performed with a solvent solution containing a control peptide (SEQ ID NO: 5, VLWCSHCMGFLWPTYT). The control peptide and the miPEP172c have the same content of amino acids, but different sequences. The treatments are performed every two days.

---

The invention claimed is:

1. A method for promoting nodulation between a plant and a bacterium comprising:
   (i) providing a plant that naturally expresses an miR comprising a nucleic acid sequence that has at least 90% sequence identity to SEQ ID NO: 1 or to SEQ ID NO: 6, wherein the miR regulates the expression of at least one gene involved in the nodulation in said plant and the plant comprises a naturally expressed miPEP that is a peptide of from 3 to 100 amino acids encoded by an open reading frame in the 5' portion of the primary transcript of the miR, and wherein the primary transcript of the miR has at least 80% sequence identity to SEQ ID NO: 4 or to SEQ ID NO: 9, and
   (ii) exogenously introducing a miPEP into the plant, wherein the miPEP is capable of modulating the accumulation of the miR in said plant and the miPEP has 100% identity with the naturally expressed miPEP, and wherein the miPEP is introduced exogenously either:
      as a peptide chosen among an isolated and/or purified peptide, a synthetic peptide and a recombinant peptide; or
      as a peptide produced in the plant following the non-natural introduction of a nucleic acid coding said miPEP in said plant, said nucleic acid not comprising the sequence of said miR.

2. The method of claim 1, wherein the miR has a nucleotide sequence consisting of SEQ ID NO: 1.

3. The method of claim 1, wherein the primary transcript of the miR has at least 90% sequence identity to SEQ ID NO: 4.

4. The method of claim 1, wherein the miR has a nucleotide sequence consisting of SEQ ID NO: 6.

5. The method of claim 1, wherein the primary transcript of the miR has at least 90% sequence identity to SEQ ID NO: 9.

6. The method of claim 1, wherein said plant is:
   (i) a leguminous plant selected from the group consisting of: lotus (*Lotus* sp.), soybean (*Glycine max*), peanut (*Arachis hypogaea*), common bean (*Phaseolus vulgaris*), pea (*Pisum sativum*), lentil (*Lens culinaris*), chickpea (*Cicer arietinum*), broad bean and field bean (*Vicia faba*), vetches (*Vicia* sp.), vetchlings (*Lathyrus* sp . . . ), alfalfa (*Medicago* sp.), clover (*Trifolium* sp.), lupin (*Lupinus* sp.), mungo bean (*Vigna radiata*), liquorice (*Glycyrrhiza glabra*), rosewood (*Dalbergia*), trefoil (*Lotus corniculatus*), sainfoin (*Onobrychis viciifolia*), rooibos (*Aspalathus linearis*), and fenugreek (*Trigonella foenum-graecum*), or
   (ii) sugar beet (*Beta vulgaris*).

7. The method of claim 1, wherein said bacterium is a bacterium from the Rhizobiacea family selected from the genera *Rhizobium, Sinorhizobium, Mesorhizobium, Bradyrhizobium* or *Azorhizobium*.

8. A method for producing a transgenic plant, comprising:
   (i) providing a plant that naturally expresses an miR comprising a nucleic acid sequence that has at least 90% sequence identity to SEQ ID NO: 1 or to SEQ ID NO: 6, wherein the miR regulates the expression of at least one gene involved in the nodulation in said plant and the plant comprises a naturally expressed miPEP that is a peptide of from 3 to 100 amino acids encoded by an open reading frame in the 5' portion of the primary transcript of the miR, wherein the primary transcript of the miR has at least 80% sequence identity to SEQ ID NO: 4 or to SEQ ID NO: 9,
   (ii) introducing a nucleic acid coding a miPEP having 100% sequence identity to the naturally expressed miPEP into a plant, or into at least a cell of said plant, in conditions allowing the expression of the miPEP, wherein the miPEP is capable of modulating the accumulation of the miR in the plant and the nucleic acid does not comprise the sequence of the miR, and
   (iii) culturing the plant, or at least a cell of said plant, obtained in step (ii) in conditions making it possible to obtain a transgenic plant.

9. The method of claim 8, wherein the miR has a nucleotide sequence consisting of SEQ ID NO: 1.

10. The method of claim 8, wherein the primary transcript of the miR has at least 90% sequence identity to SEQ ID NO: 4.

11. The method of claim 8, wherein the miR has a nucleotide sequence consisting of SEQ ID NO: 6.

12. The method of claim 8, wherein the primary transcript of the miR has at least 90% sequence identity to SEQ ID NO: 9.

13. The method of claim 8, wherein said plant is:
(i) a leguminous plant selected from the group consisting of: lotus (*Lotus* sp.), soybean (*Glycine max*), peanut (*Arachis hypogaea*), common bean (*Phaseolus vulgaris*), pea (*Pisum sativum*), lentil (*Lens culinaris*), chickpea (*Cicer arietinum*), broad bean and field bean (*Vicia faba*), vetches (*Vicia* sp.), vetchlings (*Lathyrus* sp.), alfalfa (*Medicago* sp.), clover (*Trifolium* sp.), lupin (*Lupinus* sp.), mungo bean (*Vigna radiata*), liquorice (*Glycyrrhiza glabra*), rosewood (*Dalbergia*), trefoil (*Lotus corniculatus*), sainfoin (*Onobrychis viciifolia*), rooibos (*Aspalathus linearis*), and fenugreek (*Trigonella foenum-graecum*), or
(ii) sugar beet (*Beta vulgaris*).

14. The method of claim 8, wherein said bacterium is a bacterium from the Rhizobiacea family selected from the genera *Rhizobium, Sinorhizobium, Mesorhizobium, Bradyrhizobium* or *Azorhizobium*.

15. A transgenic plant as obtained by the method as defined according to claim 8.

16. A composition suitable for inoculation of a host plant that naturally expresses an miR comprising a nucleic acid sequence that has at least 90% sequence identity to SEQ ID NO: 1 or to SEQ ID NO: 6 comprising at least:
one bacterium from the Rhizobiaceae family; and
one peptide comprising an amino acid sequence that has 100% sequence identity to a naturally expressed miPEP in the host plant, wherein (i) the miR regulates the expression of at least one gene involved in the nodulation in said plant, (ii) the miR is derived from a primary transcript having at least 80% sequence identity to SEQ ID NO: 4 or to SEQ ID NO: 9, wherein the primary transcript encodes a naturally expressed miPEP that is a peptide of from 3 to 100 amino acids encoded by an open reading frame in the 5' portion of the primary transcript of the miR, and (iii) the miPEP is capable of modulating the accumulation of the miR in said plant.

17. The composition of claim 16, wherein the miR has a nucleotide sequence consisting of SEQ ID NO: 1.

18. The composition of claim 16, wherein the primary transcript of the miR has at least 90% sequence identity to SEQ ID NO: 4.

19. The composition of claim 16, wherein the miR has a nucleotide sequence consisting of SEQ ID NO: 6.

20. The composition of claim 16, wherein the primary transcript of the miR has at least 90% sequence identity to SEQ ID NO: 9.

\* \* \* \* \*

SEQUENCE LISTING

```
<160> NUMBER OF SEQ ID NOS: 9

<210> SEQ ID NO 1
<211> LENGTH: 21
<212> TYPE: RNA
<213> ORGANISM: Glycine max

<400> SEQUENCE: 1
ggaaucuuga ugaugcugca g                                      21

<210> SEQ ID NO 2
<211> LENGTH: 16
<212> TYPE: PRT
<213> ORGANISM: Glycine max

<400> SEQUENCE: 2

Met Trp Val Leu Cys Leu Phe Cys Trp Pro Thr Tyr Thr His Gly Ser
1               5                   10                  15

<210> SEQ ID NO 3
<211> LENGTH: 51
<212> TYPE: DNA
<213> ORGANISM: Glycine max

<400> SEQUENCE: 3
atgtgggtct tgtgtttgtt ttgttggcct acatatacac atgggagttg a      51

<210> SEQ ID NO 4
<211> LENGTH: 929
<212> TYPE: DNA
<213> ORGANISM: Glycine max

<400> SEQUENCE: 4
cactctctca tctctacttg accactctct ctatatatac accactaaac cctttcttcg    60
ttctcagtta tcttctttca cttcacttaa cctagcctcc ttcccattct gatttgagtt   120
```

```
cttgctttgc ctcttaattt tattttcct cttagctttc ttcgatctta acctttgaac    180
agtaattgct tgctttgtat acattaatta ctataggtgg tactttggca gcttttctat    240
tgtatagaga cttatcagtg aataatacta ctatgtgggt cttgtgtttg ttttgttggc    300
ctacatatac acatgggagt tgaggagcct tttaggcctt agccttacat tagttgtccc    360
tctttccttg cctttacttt tgcttcatat attggatttg attagattta gggttagggt    420
tagggctgtt ctattctcct cctcctcctt ttctacttcc tgatatgctt caattcctcc    480
tctctctctc tctctcttga agttttatgt tttatggcca agtgatctta atggtggtaa    540
cacagagaga cctaatgaag tcctaaataa actaaagaaa tcagtcactg tttgccggtg    600
gagcatcatc aagattcaca agctttaggg gcattaattt gtttgaggtg gttccttatt    660
gctccaaaac caattagccc ttttgctatg ggaatcttga tgatgctgca gcagcaataa    720
atgactaata ctactaccag atattgcttg aggaggatct cactactaca caactgtgct    780
acaaggccag gagcaaagga ggttatttaa ttaactaaat aattatgtta ttaatttgtt    840
ttctaaatat tcaagaaatt ggattaggta attaccaagt tacaagccac ttttggattt    900 accttttatta actctagtag ctgataaat                                    929

<210> SEQ ID NO 5
<211> LENGTH: 16
<212> TYPE: PRT
<213> ORGANISM: Artificial sequence
<220> FEATURE:
<223> OTHER INFORMATION: Synthetic peptide

<400> SEQUENCE: 5

Val Leu Trp Cys Ser His Cys Met Gly Phe Leu Trp Pro Thr Tyr Thr
1               5                   10                  15

<210> SEQ ID NO 6
<211> LENGTH: 21
<212> TYPE: RNA
<213> ORGANISM: Glycine max

<400> SEQUENCE: 6
ugaagcugcc agcaugaucu g                                              21

<210> SEQ ID NO 7
<211> LENGTH: 17
<212> TYPE: PRT
<213> ORGANISM: Glycine max

<400> SEQUENCE: 7

Met Lys Gly Val His His Phe Phe His His Lys Tyr Val Gly Leu Arg
1               5                   10                  15

Gly

<210> SEQ ID NO 8
<211> LENGTH: 51
<212> TYPE: DNA
<213> ORGANISM: Glycine max

<400> SEQUENCE: 8
atgaaagggg ttcatcactt ttttcatcac aagtatgttg gtttgagagg t              51

<210> SEQ ID NO 9
<211> LENGTH: 665
<212> TYPE: DNA
```

```
<213> ORGANISM: Glycine max

<400> SEQUENCE: 9
gaaaaggaag tcattgtcaa tagctgtaag gaggagcaaa acctaccatt aaatactccc      60
tctatggcac agtagtgaaa gaaaagagac attgagctgc gcacaggcat tcattcatat    120
ggatcagtgt ggagataaag aggatcacga gggtctccct ttaattactc caaacatgca    180
tggcttgttc cccttttttgt taatttctat gtatcaagat gttggtaccc tctctcagga   240
tttgcttcaa tgaaaggggt tcatcacttt tttcatcaca agtatgttgg tttgagaggt    300
tgaagctgcc agcatgatct ggtaaatcac atactttttt ttttctcacc tctcatgcct    360
aatttttaag caccagtcat tagagaaaat aatggtgaaa aatccatcta ttcaattttt    420
tttttcaaat tcaaggtttc cagtatgtat cactaatggt gaaaaaagtg atggaatttt   480
gtagaacatg ggttaaattt actttttttt tttttgagtt ttcattttct tcaagtttct    540
gagccaagaa ataaaagaga cttataaatt ggaattaata cttaaaggaa acccaccaga    600
agggcaattt ggttatcata agatgtggtt tccatcaggt catcttgcag cttcaatcac    660
tcaat                                                                665
```